US006299882B1

(12) United States Patent
Junker

(10) Patent No.: US 6,299,882 B1
(45) Date of Patent: Oct. 9, 2001

(54) UL54.5 OF MAREK'S DISEASE VIRUS (MDV)

(75) Inventor: David E. Junker, San Diego, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/289,254

(22) Filed: Apr. 9, 1999

(51) Int. Cl.$^7$ .......................... A61K 39/12; A61K 39/245

(52) U.S. Cl. .................................... 424/199.1; 424/229.1; 435/320.1; 435/235.1; 435/69.1; 435/69.3; 536/23.72

(58) Field of Search .............................. 424/199.1, 229.1, 424/816; 435/235.1, 320.1, 69.1, 69.3; 536/23.72

(56) References Cited

U.S. PATENT DOCUMENTS

| | | | |
|---|---|---|---|
| 5,151,267 | 9/1992 | Babiuk et al. | 424/89 |
| 5,399,346 | 3/1995 | Anderson et al. | 424/93.21 |
| 5,853,733 * | 12/1998 | Cochran et al. | 424/199.1 |

FOREIGN PATENT DOCUMENTS

| | | | |
|---|---|---|---|
| 0 259 149 B1 | 9/1997 | (EP) | A61K/39/15 |
| WO 96/05291 | 2/1996 | (WO) | C12N/5/10 |

OTHER PUBLICATIONS

Tsushima et al . Virus Research, 1999, vol. 60, pp. 101–110.*

Ren et al . Virology, 1994, 204 (1), 242–250.*

Ono et al . Virology, 1994, 201 (1), 142–146.*

Sondermeijer et al . Vaccine, 1993, vol. 11, No. 3, pp. 349–358.*

Gubler et al., "A simple and very efficient method for generating cDNA libraries," *Gene*, vol. 25, pp. 263–269 (1983).

Izumiya et al., "Identification and transcriptional analysis of homologues of the herpes simplex virus type 1 UL41 to UL51 genes in the genome of nononcogenic Marek's disease virus serotype 2," *Journal of General Virology*, vol. 79, pp. 1997–2001 (1998).

Kawai et al., "New Procedure for DNA Transfection with Polycation and Dimethyl Sulfoxide," *Molecular and Cellular Biology*, pp. 1172–1174 (1984).

Laemmli U.K., "Cleavage of Structural Proteins during the Assembly of the Head of Bacteriophage T4," *Nature*, vol. 227, pp. 680–685 (1970).

Schraf, S.J., "Cloning with PCR," *PCT Protocols: A Guide to Methods and Applications*, Ch. 11, pp.84–90 (1990).

* cited by examiner

*Primary Examiner*—Ali R. Salimi
(74) *Attorney, Agent, or Firm*—Pamela G. Salkeld; Sandy S. Zaradic

(57) ABSTRACT

The present invention provides methods and reagents for inducing active immunity in animals. In particular, the present invention provides recombinant herpesviruses having foreign DNA that are capable of inducing immunity to the herpesvirus and/or the source of the foreign DNA. The present invention also provides mutant herpesviruses having portions of their genome deleted. Preferably, foreign DNA is introduced, or portions of the genome are deleted, in the UL54.5 open reading frame of avian herpesviruses or the UL43 open reading frame of Marek's disease virus.

12 Claims, 6 Drawing Sheets

UL54.5 OF MAREK'S DISEASE VIRUS (MDV)

Throughout this disclosure, various publications, patents and patent applications are referenced. The disclosures of these publications, patents and patent applications are herein incorporated by reference.

FIELD OF THE INVENTION

The present invention relates to viral vectors for vaccination of animals. In particular, the present invention pertains to viral vectors having gene insertion sites for the introduction of foreign DNA.

BACKGROUND

Marek's disease is a lymphoproliferative disease of chickens caused by Marek's disease virus (MDV). MDV, a naturally occurring herpesvirus, infects bursa-derived and thymus-derived lymphocytes in chickens, and may subsequently induce a lymphoma of thymus-derived lymphocytes. MDV is a designation of a family of avian herpesviruses. For example, MDV1 is a virulent strain of herpesvirus in chickens, MDV2 is a naturally attenuated herpesvirus strain in chickens, and MDV3 is a nonpathogenic herpesvirus of turkey.

Since Marek's disease is contagious, the virus has become an important pathogen of chickens, particularly in an environment of large scale breeding such as in the poultry industry. Currently, Marek's disease is controlled by vaccination of embryos at 17–19 days of incubation, or one day old chicks.

The application of recombinant DNA techniques to animal viruses in general has a recent history. The first viruses to be engineered have been those with the smallest genomes. For example, in the case of the papovaviruses, because these viruses are so small and cannot accommodate much extra DNA, their use in genetic engineering has been as defective replicons. Thus, foreign DNA sequence expression from these viruses requires a wild-type helper virus and is limited to cell culture systems. On the other hand, for adenoviruses, there is a small amount of nonessential DNA that can be replaced by foreign sequences. This technique has also been applied to portions of the herpesvirus genome in an avian herpesvirus (see U.S. Pat. No. 5,853,733 to Cochran et al).

The cases of deletion or insertion of genes into herpesviruses demonstrate that it is possible to genetically engineer herpesvirus genomes by recombinant DNA techniques. In the past, the methods that have been used to insert genes involve homologous recombination between the viral DNA cloned in plasmids and purified viral DNA transfected into the same animal cell. However, the extent to which one can generalize the location of the deletion and the sites for insertion of foreign DNA sequences is not known from these previous studies.

The identification of suitable DNA sequence insertions sites in avian herpesviruses are valuable for the development of new vaccines. The selection of (i) a suitable virus and (ii) the particular portion of the genome to use as an insertion site for creating a vector for foreign DNA sequence expression, however, pose a significant challenge. In particular, the insertion site must be non-essential for the viable replication of the virus, as well as its operation in tissue culture and in vivo. Moreover, the insertion site must be capable of accepting new genetic material, while ensuring that the virus continues to replicate.

What is needed is the identification of novel viruses and gene insertion sites for the creation of new viral vectors.

SUMMARY OF THE INVENTION

The present invention provides mutant and recombinant herpesviruses comprising a foreign DNA sequence inserted into a site in the herpesvirus genome. In one embodiment, the site is non-essential for viral replication. In a preferred embodiment, the foreign DNA sequence is capable of being expressed in a host cell infected with the recombinant herpesvirus and its expression. In a particularly preferred embodiment, the foreign DNA sequence is also under control of a promoter located upstream of the foreign DNA sequence.

The present invention is not limited to particular sites for insertion or deletion. In one embodiment, the deletion and/or insertion is in the UL54.5 open reading frame of a Marek's disease virus. In another embodiment, the deletion and/or insertion is in the UL43 open reading frame of a Marek's disease virus. In a preferred embodiment, the insertion is in the genome of Marek's disease virus type 1.

While not limited to particular types of DNA inserted, in one embodiment of the present invention the foreign DNA sequence inserted into the herpesvirus genome encodes a polypeptide. Preferably, the polypeptide is immunogenic to the animal into which the recombinant herpesvirus is introduced. Preferably, this immunogenic polypeptide is a linear polymer of more than 10 amino acids linked by peptide bonds which stimulates the animal to produce antibodies. In a preferred embodiment, the foreign DNA sequence also encodes a detectable marker. Preferably, the detectable marker is $E.\ coli$ B-galactosidase.

In preferred embodiments, the recombinant herpesvirus contains a foreign DNA sequence encoding an immunogenic polypeptide from chicken anemia virus (CAV), infectious bursal disease virus (IBDV), Marek's disease virus (MDV), Newcastle disease virus (NDV), infectious iaryngotracneitis virus (ILTV), or infectious bronchitis virus (IBV), fragments thereof and/or substantially homologous sequences. In another preferred embodiment, the foreign DNA encodes a cytokine. The present invention also contemplates recombinant herpesviruses having more than one foreign DNA sequence encoding an antigen or antigens.

When the foreign DNA sequence of the recombinant herpesvirus of the present invention encodes an immunogenic polypeptide from infectious bursal disease virus (IBDV), it is preferred that the immunogenic polypeptide is IBDV VP2, VP3 or VP4 protein, fragments thereof and/or substantially homologous sequences. When the foreign DNA sequence encodes an immunogenic polypeptide from MDV. Preferably, the immunogenic polypeptide is MDV glycoprotein B (gB), glycoprotein D (gD), or glycoprotein A (gA) fragments thereof and/or substantially homologous sequences.

When the foreign DNA sequence encodes an immunogenic polypeptide from Newcastle disease virus (NDV), it is preferred that the immunogenic polypeptide is NDV fusion (F) protein or NDV hemagglutinin-neuraminidase (HN), fragments thereof and/or substantially homologous sequences.

When the foreign DNA sequence encodes an immunogenic polypeptide from infectious laryngotracheitis virus (ILTV), it is preferred that the immunogenic polypeptide is ILTV glycoprotein "B" (gB), ILTV glycoprotein D (gD), or ILTV glycoprotein I (gI), fragments thereof and/or substantially homologous sequences.

When the foreign DNA sequence encodes an immunogenic polypeptide from infectious bronchitis virus (IBV), it is preferred that the immunogenic polypeptide is IBV spike protein, IBV matrix protein, nucleocapsid protein, fragments thereof and/or substantially homologous sequences.

The expression of the inserted foreign DNA sequence can be under control of a promoter located upstream of the foreign DNA sequence. Preferably, the promoter is a herpesvirus promoter. More preferably, the promoter is selected from a group consisting of pseudorabies virus (PRV) gX promoter, MDV gB promoter, MDV gA promoter, MDV gD promoter, ILTV gB promoter, ILTV gD promoter, ITLV gI promoter, human cytomegalovirus virus (HCMV) immediate early promoter, and/or substantially homologous sequences.

The present invention further provides for a homology vector for producing a recombinant herpesvirus by inserting a foreign DNA sequence into the herpesvirus genome. In one embodiment, the homology vector comprises a double-stranded DNA molecule consisting essentially of a double-stranded foreign DNA sequence, with at one end of the foreign DNA sequence, double-stranded DNA homologous to the genomic DNA located at one side of a non-essential site of the herpesvirus genome, and at the other end of the foreign DNA sequence, double-stranded DNA homologous to the herpesvirus genomic DNA sequence located at the other side of the same site. In such an embodiment, the double-stranded DNA can be homologous to a DNA sequence present within a 3212 base pair Sac I to Bgl II subfragment contained within the Bam HI "B" genomic fragment of a Marek's disease virus type 1. Preferably, a DNA sequence corresponding to a promoter is located upstream of the foreign DNA sequence and controls its expression. Likewise, it is preferable that the foreign DNA sequence encode an immunogenic polypeptide (e.g. those described above).

In one embodiment of the invention, the double-stranded herpesvirus DNA is homologous to DNA sequence present within the Bam HI "B" fragment of the MDV herpesvirus genome. Preferably, the double-stranded herpesvirus DNA is homologous to DNA sequences present within the open reading frame encoding UL 43 protein of the herpesvirus genome. In another embodiment of the invention, the double-stranded herpesvirus DNA is homologous to DNA sequences present within the Bam HI "M" fragment of a herpesvirus genome. Preferably, the double-stranded herpesvirus DNA is homologous to DNA sequence present within the UL54.5 gene coding region of a herpesvirus genome.

The invention further provides a vaccine which comprises an effective immunizing amount of a recombinant or mutant herpesvirus of the present invention and a suitable carrier.

The present invention further provides a method of immunizing an animal. A preferred animal to be immunized is a fowl.

The present invention also provides a method of immunizing a fowl in ovo. For the purposes of this invention, this includes immunizing a fowl against infectious bursal disease virus, Marek's disease virus, Newcastle disease virus, infectious laryngotracheitis virus, or infectious bronchitis virus. Preferably, the method comprises administering to the fowl an effective immunizing dose of the vaccine of the present invention. The vaccine may be administered by any of the methods well known to those skilled in the art, for example, by intramuscular, subcutaneous, intraperitoneal or intravenous, injection. Alternatively, the vaccine may be administered intranasally, orally or intraocularly.

The present invention also provides a host cell infected with a recombinant herpesvirus of the present invention. Preferably, the host cell is an avian cell.

DEFINITIONS

For purposes of this invention, a "host cell" is a cell used to propagate a vector and its insert. Infecting the cell can be accomplished by methods well known to those skilled in the art, for example, as set forth in DNA Transfection For Generating Recombinant Herpesvirus 11) below.

The term, "animal" refers to organisms in the animal kingdom. Thus, this term includes humans, as well as other organisms. Preferably, the term refers to vertebrates. More preferably, the term refers to avian animals.

An "effective immunizing amount" of recombinant herpesvirus of the present invention is within the range of $10^2$ to $10^9$ Plaque Forming Units (PFU)/dose.

For purposes of this invention, a "homology vector" is a plasmid constructed to insert foreign DNA sequence in a specific site on the genome of a herpesvirus.

A "foreign DNA sequence" is a segment of DNA that has been or will be attached to another DNA molecule using recombinant techniques wherein that particular DNA segment is not found in association with the other DNA molecule in nature. The source of such foreign DNA may or may not be from a separate organism than that in which it is placed. The foreign DNA may also be a synthetic sequence having codons different from the native gene. Examples of recombinant techniques include, but are not limited to, the use of restriction enzymes and ligases to splice DNA.

An "insertion site" is a restriction site in a DNA molecule into which foreign DNA can be inserted.

A "replication competent virus" is a virus whose genetic material contains all of the DNA or RNA sequences necessary for viral replication as are found in a wild-type of the organism. Thus, a replication competent virus does not require a second virus or a cell line to supply something defective in or missing from the virus in order to replicate. A "non-essential site in the herpesvirus genome" means a region in the herpesvirus genome, the polypeptide product of which is not necessary for viral infection or replication.

A "vector" is a replicon, such as a plasmid, phage, cosmid or virus, to which another DNA sequence may be attached so as to bring about the expression of the attached DNA sequence.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found in linear DNA molecules (e.g., restriction fragments of DNA from viruses, plasmids, and chromosomes).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, viral DNA, and even synthetic DNA sequences. A polyadenylation signal and transcription termination sequence can be located 3' to the coding sequence.

A "promoter sequence" is a DNA regulatory region capable of binding RNA polymerase or an auxiliary protein in a cell and initiating transcription of a downstream (3' direction) coding sequence. For purposes of defining the present invention, the promoter sequence is in close proximity to the 3' terminus by the translation start codon (ATG) of a coding sequence and extends upstream (5' direction) to include the minimum number of bases or elements necessary to facilitate transcription at levels detectable above background. Within the promoter sequence will be found a transcription initiation site, as well as protein binding domains (consensus sequences) responsible for the binding of RNA polymerase. Eucaryotic promoters will often, but not always, contain "TATA" boxes and "CAAT" boxes, conserved sequences found in the promoter region of many eucaryotic organisms.

A coding sequence is "operably linked to" or "under the control of" control sequences in a cell when RNA polymerase will interact with the promoter sequence directly or indirectly and result in the transcription of the coding sequence into mRNA, which is then translated into the polypeptide encoded by the coding sequence.

Two polypeptide sequences are "substantially homologous" when at least about 80% (preferably at least about 90%, and most preferably at least about 95%) of the amino acids match over a defined length of the molecule.

Two DNA sequences are "substantially homologous" when they are identical to or not differing in more that 40% of the nucleotides, more preferably about 20% of the nucleotides, and most preferably about 10% of the nucleotides.

A virus that has had a foreign DNA sequence inserted into its genome is a "recombinant virus," while a virus that has had a portion of its genome removed by intentional deletion (e.g., by genetic engineering) is a "mutant virus."

The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Antigenic" refers to the ability of a molecule containing one or more epitopes to stimulate an animal or human immune system to make a humoral and/or cellular antigen-specific response. An "antigen" is an antigenic polypeptide.

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polypeptide" and "immunogenic amino acid sequence" refer to a polypeptide or amino acid sequence, respectively, which elicit antibodies that neutralize viral infectivity, and/or mediate antibody-complement or antibody dependent cell cytotoxicity to provide protection of an immunized host. An "immunogenic polypeptide" as used herein, includes the full length (or near full length) sequence of the desired protein or an immunogenic fragment thereof.

By "immunogenic fragment" is meant a fragment of a polypeptide which includes one or more epitopes and thus elicits antibodies that neutralize viral infectivity, and/or mediates antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the antigens.

By "infectious" is meant having the capacity to deliver the viral genome into cells.

The term "open reading frame" or "ORF" is defined as a genetic coding region for a particular gene that, when expressed, can produce a complete and specific polypeptide chain protein.

The term "avian herpesvirus" connotes a herpesvirus that is capable of replicating in avian hosts and do not naturally replicate in other host animals.

DETAILED DESCRIPTION OF THE INVENTION

Figure 1:
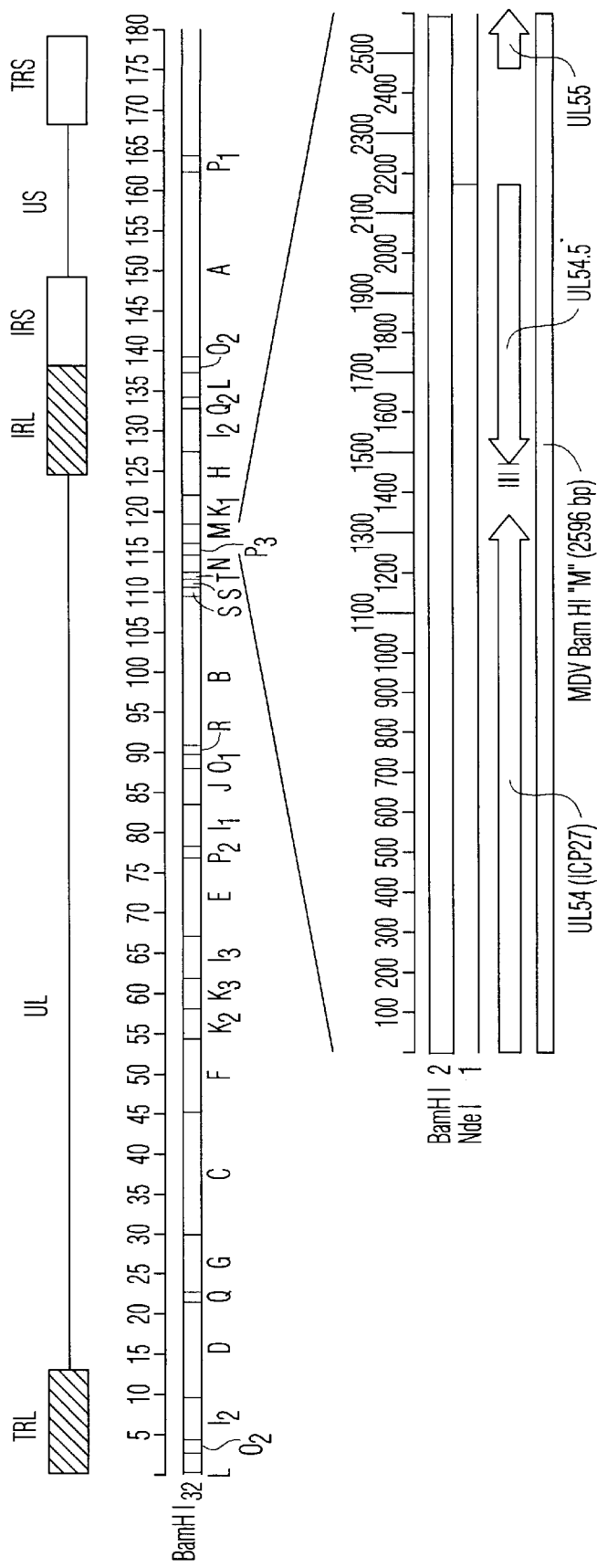
FIG. 1 is a BamH1 restriction map of an MDV genome particularly pointing out the location of an "M" fragment.
Figure 2:
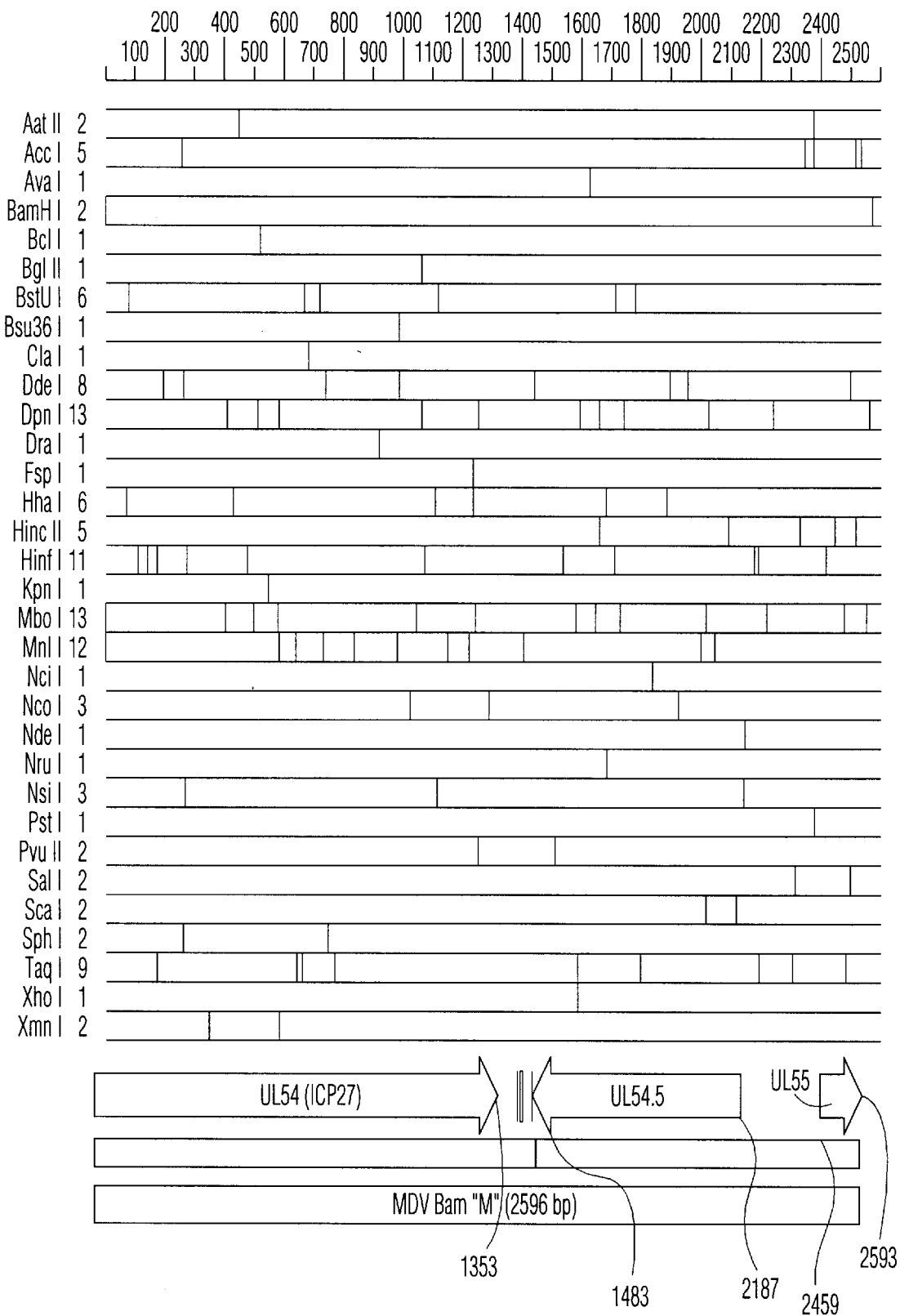
FIG. 2 is a map designating the open reading frames in the BamH1 "M" fragment of an MDV genome.

The methods and compositions of the present invention involve modifying cloned DNA sequences from various prokaryotic and eucaryotic sources and by insertions, deletions, single or multiple base changes, and subsequent insertions of these modified sequences into the genome of a herpesvirus. One example includes cloning parts of a herpesvirus DNA into plasmids in bacteria, reconstructing the virus DNA while in the cloned state so that the DNA contains deletions of certain sequences, and/or furthermore adding foreign DNA sequences either in place of the deletions or at sites removed from the deletions. The methods and compositions of the present invention also involve the deletion of a portion of the genome of a herpesvirus to produce a mutant virus.

Generally, the foreign gene construct is cloned into a nucleotide sequence which represents only a part of the entire herpesvirus genome, which may have one or more appropriate deletions. This chimeric DNA sequence is usually present in a plasmid which allows successful cloning to produce many copies of the sequence. The cloned foreign gene construct can then be included in the complete viral genome, for example, by in vivo recombination following a DNA-mediated cotransfection technique. Multiple copies of a coding sequence or more than one coding sequences can be inserted so that the recombinant vector can express more than one foreign protein. The foreign gene can have additions, deletions or substitutions to enhance expression and/or immunological effects of the expressed protein.

In order for successful expression of the gene to occur, it can be inserted into an expression vector together with a suitable promoter including enhancer elements and polyadenylation sequences. A number of eucaryotic promoter and polyadenylation sequences which provide successful expression of foreign genes in mammalian cells and how to construct expression cassettes, are known in the art, for example in U.S. Pat. No. 5,151,267. The promoter is selected to give optimal expression of immunogenic protein which in turn satisfactorily leads to humoral, cell mediated and mucosal immune responses according to known criteria.

The foreign protein produced by expression in vivo in a recombinant virus-infected cell may be itself immunogenic. More than one foreign gene can be inserted into the viral genome to obtain successful production of more than one effective protein.

Therefore, one utility of the use of a mutant herpesvirus or the addition of a foreign DNA sequence into the genome of a herpesvirus is to vaccinate an animal. For example, a mutant virus could be introduced into an animal to elicit an immune response to the mutant virus.

Alternatively, a recombinant herpesvirus having a foreign DNA sequence inserted into its genome that encodes a polypeptide may also serve to elicit an immune response in an animal to the foreign DNA sequence, polypeptide encoded by the foreign DNA sequence and/or herpesvirus. Such a virus may also be used to introduce foreign DNA and its products into the host animal to alleviate a defective genomic condition in the host animal. These recombinant herpesviruses are referred to as viral vectors when it is a virus that can carry the foreign DNA in the host animal.

The present invention is not limited to the use of a particular herpesvirus vector. One avian herpesvirus suitable for use as a viral vector is MDV. To provide for MDV as a vector and vaccine against Marek's Disease, it is desirable to locate a site within the MDV genome which is not essential for viral replication and function; and into which can be inserted one or more endogenous genes encoding an MDV antigen(s) to further stimulate the immune response against the encoded antigen(s). On the other hand, to provide for MDV as a viral vector or as an expression vector for use as a multivalent vaccine, it is desirable to locate a site within the MDV genome which is not essential for viral replication and function; and into which can be inserted one or more exogenous genes encoding an antigen(s) of a poultry pathogen other than MDV to further stimulate the immune response against MDV and such other poultry pathogens. Alternatively, a combination of copies of endogenous genes and exogenous genes may be inserted into a nonessential region of such viral vector.

When an MDV genome is used, it is preferred that an attenuated MDV type 1 strain be used. Rispens CVI-988 is an attenuated serotype 1 MDV vaccine strain that can be used to provide protection against very virulent strains of MDV.

This MDV genome is a linear 180 kilobase pair double stranded molecule consisting of two unique regions: a unique short region (US), and a unique long region (UL). Each of the unique regions is flanked by inverted repeats: a long terminal repeat (TRL) and internal long inverted repeat (IRL) for UL, and a short internal inverted repeat (IRS) and short terminal repeat (TRS) for US.

While the present invention is not limited to particular DNA deletion and/or insertion sites, it has been discovered that the UL43 region and UL54.5 region of avian herpesviruses contain appropriate sites for deletion and insertion. For example, there is an Xho I site within the UL43 region of avian herpesviruses, and in particular within the MDV genome. There is also an open reading frame (ORF) that is flanked by the UL54 and UL55 regions. This ORF, designated as UL54.5, contains an Nde I site suitable for deletion and insertion.

In particular, there is a 3212 base pair Sac I to Bgl II subfragment contained within the Bam HI "B" genomic fragment of Marek's disease virus type 1. A preferred deletion and/or insertion site within the 3212 base pair Sac I to Bgl II subfragment contained within the Bam HI "B" genomic fragment lies within an open reading frame encoding herpesvirus UL43 and a preferred insertion site insertion site within that open reading frame is a Xho I restriction endonuclease site.

Likewise, deletions and/or insertions can be placed in the Bam HI "M" genomic fragment of the herpesvirus genome. A preferred insertion site within Bam HI "M" genomic fragment lies within an open reading frame encoding herpesvirus UL54.5 and a preferred insertion site insertion site within that open reading frame is a Nde I restriction endonuclease site. In a particularly preferred embodiment, the product of the UL54.5 open reading frame is nonessential for viral replication.

Various foreign DNA sequences or coding sequences (viral, prokaryotic, and eucaryotic) can be inserted in the herpesvirus nucleotide sequence, e.g., DNA, in accordance with the present invention, particularly to provide protection against a wide range of diseases and many such genes are already known in the art. While not limited to any particular foreign DNA sequence, typically the foreign DNA sequence of interest will be derived from pathogens that in avian cause diseases that have an economic impact on the poultry industry. The genes may be derived from organisms for which there are existing vaccines, and because of the novel advantages of the vectoring technology the herpesvirus derived vaccines will be superior. Also, the gene of interest may be derived from pathogens for which there is currently no vaccine but where there is a requirement for control of the disease. Typically, the gene of interest encodes immunogenic polypeptides of the pathogen, and may represent surface proteins, secreted proteins and structural proteins.

A relevant avian pathogen that is a target for herpesvirus vectoring is Infectious Laryngotracheitis virus (ILTV). ILTV is a member of the herpesviridiae family, and this pathogen causes an acute disease of chickens which is characterized by respiratory depression, gasping and expectoration of bloody exudate.

Another target for the herpesvirus vectoring approach is Newcastle disease, an infectious highly contagious and debilitating disease that is caused by the Newcastle disease virus (NDV). NDV is a single-stranded RNA virus of the paramyxovirus family. The various pathotypes of NDV (velogenic, mesogenic, lentogenic) differ with regard to the severity of the disease, the specificity and symptoms, but most types seem to infect the respiratory system and the nervous system. NDV primarily infects chickens, turkeys and other avian species.

The present invention is also not limited to the use of a particular DNA sequence from an organism. Often selection of the foreign DNA sequence for insertion into a herpesvirus genome is based upon the protein it encodes. Preferably, the foreign DNA sequence encodes an immunogenic polypeptide. The preferred immunogenic polypeptide to be expressed by the virus systems of the present invention contain full-length (or near full-length) sequences encoding antigens. Alternatively, shorter sequences that are immunogenic (i.e., encode one or more epitopes) can be used. The shorter sequence can encode a neutralizing epitope, which is defined as an epitope capable of eliciting antibodies that neutralize virus infectivity in an i n vitro assay. Preferably the peptide should encode a protective epitope that is capable of raising in the host an protective immune response; i.e., an antibody- and/or a cell-mediated immune response that protects an immunized host from infection. In some cases the gene for a particular antigen can contain a large number of introns or can be from an RNA virus, in these cases a complementary DNA copy (cDNA) can be used.

It is also possible that only fragments of nucleotide sequences of genes can be used (where these are sufficient to generate a protective immune response) rather than the complete sequence as found in the wild-type organism. Where available, synthetic genes or fragments thereof can also be used. However, the present invention can be used with a wide variety of genes, fragment and the like, and is not limited to those set out herein.

Thus, the antigens encoded by the foreign DNA sequences used in the present invention can be either native or recombinant immunogenic polypeptides or fragments. They can be partial sequences, full-length sequences, or even fusions (e.g., having appropriate leader sequences for the recombinant host, or with an additional antigen sequence for another pathogen).

In a preferred embodiment, the mutant viruses and viral vectors of the present invention are replication competent. In this manner, the deletion from and/or insertion into the herpesvirus gnome does not destroy its ability to replicate. However, if the deletion and/or insertion does destroy or significantly inhibit the ability of the herpesvirus to replicate, the present invention contemplates the use of recombinant cell lines by constructing an expression cassette comprising a herpesvirus of the present invention and transforming host cells therewith to provide cell lines or cultures expressing proteins encoded by the deleted or disrupted DNA sequences.

These recombinant cell lines are capable of allowing a recombinant herpesvirus that is not replication competent to replicate and express the desired foreign DNA sequence or fragment thereof which is encoded within the recombinant herpesvirus. These cell lines are also extremely useful in generating recombinant herpesvirus, by in vivo recombination following DNA-mediated cotransfection.

When the methods and compositions of the present invention are used for vaccination, it is not limited to any particular administration. One example is parenteral administration. When administered parenterally, the vaccines can include the use of a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in European Patent Pub. No. 0259149.

The vaccines can also be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity in combination with systemic immunity, which plays an important role in protection against pathogens infecting the gastrointestinal tract.

In addition, the vaccine be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of the vaccine composition in a dose effective to elicit an antibody and/or T-cell mediated immune response to the immunogenic fragment. Within wide limits, the dosage is not believed to be critical.

Typically, the vaccine composition is administered in a manner which will deliver between about 1 to about 1,000 micrograms of the subunit antigen in a convenient volume of vehicle, e.g., about 1–10 cc. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations if needed. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

A recombinant herpesvirus of the present invention can also provide a way for distinguishing an animal vaccinated with the vaccine of the present invention from an animal infected with a naturally-occurring, wild-type infectious herpesvirus or other pathogen. This is possible because recombinant herpesvirus contain foreign DNA which encodes a limited number of antigens from the above mentioned viruses that are needed to confer protective immunity to the corresponding pathogens. Consequently, host animals vaccinated with those recombinant herpesviruses can be distinguished from ones which have been infected with wild-type infectious bursal disease virus, Marek's disease virus, Newcastle disease virus, infectious laryngotracheitis virus, or infectious bronchitis virus by the absence of antigens that are normally present in the wild type viruses. Moreover, when the herpesvirus vector contains a deletion of a portion of its genome that encodes an immunogenic polypeptide, the lack of an immune response from the vaccinated animal to the product of the deleted portion will indicate a vaccinated animal.

The invention also includes a method for providing gene therapy to an animal in need thereof to control a gene deficiency which comprises administering to said animal a live recombinant herpesvirus containing a foreign nucleotide sequence encoding a non-defective form of said gene under conditions wherein the recombinant virus vector genome is incorporated into said mammalian genome or is maintained independently and extrachromosomally to provide expression of the required gene in the target organ or tissue.

These kinds of techniques are used by those of skill in the art to replace a defective gene or portion thereof. For example, U.S. Pat. No. 5,399,346 to Anderson et al describes techniques for gene therapy. Moreover, examples of foreign DNA sequences nucleotide sequences or portions thereof that can be incorporated for use in a conventional gene therapy include, cystic fibrosis transmembrane conductance regulator gene, human minidystrophin gene, alphal-antitrypsin gene and the like.

Methods for constructing, selecting and purifying recombinant herpesvirus are detailed below in the Examples below. The following examples serve to illustrate certain preferred embodiments and aspects of the present invention and are not to be construed as limiting the scope thereof.

EXAMPLES

Example 1

Preparation of Marek's Disease Virus (MDV-1) Stock

Marek's disease virus stock samples were prepared by infecting tissue culture cells at a multiplicity of infection of 0.01 PFU/cell in a 1:1 mixture of HAM'S F10 and 199 medium containing 2 mM glutamine, 100 units/ml penicillin, 100 units/ml streptomycin (these components are obtained from Sigma or an equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. Infected cells were resuspended in complete medium containing 20% fetal bovine serum, 10% DMSO and stored frozen at −70° C.

Example 2

Preparation of Marek's Disease Virus (MDV-1) DNA

All manipulations of Marek's disease virus were made using strain GA5 (ATCC #624) or Rispens CVI-988 (Vineland Labs). For the preparation of MDV viral DNA from the cytoplasm of infected cells, primary chicken embryo fibroblasts were infected at a MOI sufficient to cause extensive cytopathic effect before the cells overgrew. All incubations were carried out at 39° C. in a humidified incubator with 5% $CO_2$ in air. Best DNA yields were obtained by harvesting monolayers which were maximally infected, but showing incomplete cell lysis (typically 5–7 days). Infected cells were harvested by scraping the cells into the medium using a cell scraper. The cell suspension was centrifuged at 3000 rpm for 10 minutes at 5° C. in a GS-3 rotor.

The resultant pellet was resuspended in cold PBS (20 ml/roller bottle) and subjected to another centrifugation for 10 minutes at 3000 rpm in the cold. After decanting the PBS, the cellular pellet was resuspended in 4 ml/roller bottle of RSB buffer (10 mM Tris pH 7.5, 1 mM EDTA, and 1.5 mM $MgCl_2$). NP40 (Nonidet P-40; Sigma) was added to the sample to a final concentration of 0.5% minutes with occasional mixing. The sample was centrifuged for 10 minutes at 3000 rpm in the cold to pellet the nuclei and remove cellular debris. The supernatant fluid was carefully transferred to a 15 ml Corex centrifuge tube. Both EDTA (0.5M pH 8.0) and SDS (sodium dodecyl sulfate; stock 20%) were added to the sample to final concentrations of 5 mM and 1%, respectively. One hundred microliters of proteinase-K (10 mg/ml; Boehringer Mannheim) was added per 4 ml of sample, mixed, and incubated at 45° C. for 1–2 hours. After this period, an equal volume of water-saturated phenol was added to the sample and gently mixed by hand. The sample was spun in a clinical centrifuge for 5 minutes at 3000 rpm to separate the phases. NaAc was added to the aqueous phase to a final concentration of 0.3M (stock solution 3M pH 5.2), and the nucleic acid precipitated at −70° C. for 30 minutes after the addition of 2.5 volumes of cold absolute ethanol. DNA in the sample was-pelleted by spinning for 20 minutes to 8000 rpm in an HB-4 rotor at 5° C. The supernatant was carefully removed and the DNA pellet washed once with 25 ml of 80% ethanol. The DNA pellet was dried briefly by vacuum (2–3 minutes), and resuspended in 50 microliters/roller bottle of infected cells of TE buffer (10 mM Tris pH 7.5, 1 mM EDTA). Typically, yields of viral DNA ranged between 5–10 micrograms/roller bottle of infected cells. All viral DNA was stored at approximately 10° C.

Example 3

DNA Sequencing

DNA sequencing was performed by flourescent labeled dideoxy sequencing reactions using ABI PRISM Dye Terminator Cycle Sequencing Ready Reaction Kit with Amplitaq DNA polymerase, FS (Perkin-Elmer; per manufacturer's instructions) and electrophoresed on an Perkin-Elmer/Applied Biosystems automated DNA sequencer Model 373A according to manufacturer's instructions. Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using DNAStar software.

Example 4

Molecular Biological Techniques

Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by J. Sambrook et al., *Molecular Cloning A Laboratory Manual Second Edition*, Cold Spring Harbor Press, 1989 and *Current Protocols in Molecular Biology* (1992) John Wiley & Son's, Inc. Except as noted, these were used with minor variation.

Example 5

Polymerase Fill-In Reaction

DNA was resuspended in buffer containing 50 mM Tris pH 7.4, 50 mM KCl, 5 mM $MgCl_2$, and 400 micromolar each of the four deoxynucleotides. Ten units of Klenow DNA polymerase (BRL) were added and the reaction was allowed to proceed for 15 minutes at room temperature. The DNA was then phenol extracted and ethanol precipitated as above.

Example 6

Cloning With The Polymerase Chain Reaction

The polymerase chain reaction (PCR) was used to introduce restriction sites convenient for the manipulation of various DNAs. The procedures used are described by M. A.

Innis et al., *PCR Protocols A Guide to Methods and Applications*, 84–91, Academic Press, Inc., San Diego, 1990.). In general, amplified fragments were less than 500 base pairs in size and critical regions of amplified fragments were confirmed by DNA sequencing. The primers used in each case are detailed in the descriptions of the construction of homology vectors below.

Example 7

Preparation Of Infected Cell Lysates

A confluent monolayer of secondary chicken embryo fibroblasts cells in a 25 cm$^2$ flask or a 60 mm petri dish was infected with 100 microliters of virus sample. After cytopathic effect was complete, the medium and cells were harvested and the cells were pelleted at 3000 rpm for 5 minutes in a clinical centrifuge. The cell pellet was resuspended in 250 microliters of disruption buffer (2% sodium dodecyl sulfate, 2% β-mercapto-ethanol). The samples were sonicated for 30 seconds on ice and stored at −20° C.

Example 8

Western Blotting Procedure

Samples of lysates and protein standards were run on a polyacrylamide gel according to the procedure of Laemnli, U.K. (1970) Nature 277:680. After gel electrophoresis the proteins were transferred and processed according to Sambrook et al. (1989). The primary antibody was diluted 1:100 with 5% non-fat dry milk in Tris-sodium chloride, and sodium azide (TSA: 6.61 g Tris-HCl, 0.97 g Tris-base, 9.0 g NaCl and 2.0 g Sodium Azide per liter H$_2$O). The secondary antibody was alkaline phosphatase conjugated and diluted 1:1000 with TSA.

Example 9 cDNA Cloning Procedure cDNA cloning refers to the methods used to convert RNA molecules into DNA molecules following state of the art procedures. Applicants' methods are described in (U. Gubler and B. J Hoffman, Gene 25, 263–269). Bethesda Research Laboratories (Gaithersburg, Md.) have designed a cDNA Cloning Kit that is very similar to the procedures used by applicants, and contains a set of reagents and protocols that may be used to duplicate our results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4M guanidine thiocyanate, 0.1% antifoam A, 25 mM sodium citrate pH 7.0, 0.5% N-lauryl sarcosine, 0.1M β-metcaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7M CsCl, 25 mM sodium citrate pH 7.0) in Beckman SW41 centrifuge tube. The samples were centrifuged for 18 hrs at 20° C. at 36000 rpm in a Beckman SW41 rotor. The tubes were put on ice and the supernatants from the tubes were carefully removed by aspiration to leave the RNA pellet undisturbed. The pellet was resuspended in 400 microliters glass distilled water, and 2.6 mls of guanidine solution (7.5M guanidine-HCL, 25 mM sodium citrate pH 7.0, 5 mM dithiothreitol) were added. The 0.37 volumes of 1M acetic acid were added, followed by 0.75 volumes of cold ethanol and the sample was put at −20° C. for 18 hrs to precipitate RNA. The precipitate was collected by centrifugation in a Sorvall centrifuge for 10 min at 4° C. at 10000 rpm in an SS34 rotor. The pellet was dissolved in 1.0 ml distilled water, recentrifuged at 13000 rpm, and the supernatant saved. RNA was re-extracted from the pellet 2 more times as above with 0.5 ml distilled water, and the supernatants were pooled. A 0.1 volume of 2M potassium acetate solution was added to the sample followed by 2 volumes of cold ethanol and the sample was put at −20° C. for 18 hrs. The precipitated RNA was collected by centrifugation in the SS34 rotor at 40° C. for 10 min at 10000 rpm. The pellet was dissolved in 1 ml distilled water and the concentration taken by absorption at A260/280. The RNA was stored at −70° C.

mRNA containing polyadenylate tails (poly-A) was selected using oligo-dT cellulose (Pharmacia #27 5543-0). Three mg of total RNA was boiled and chilled and applied to the 100 mg oligo-dT cellulose column in binding buffer (0.1M Tris pH 7.5, 0.5M LiCl, 5 mM EDTA pH 8.0, 0.1% lithium dodecyl sulfate). The retained poly-A RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hrs. The RNA was resuspended in 50 microliters distilled water.

Ten micrograms poly-A RNA was denatured in 20 mM methyl mercury hydroxide for 6 min at 22° C. β-mercaptoethanol was added to 75 mM and the sample was incubated for 5 min at 22° C. The reaction mixture for first strand cDNA synthesis in 0.25 ml contained 1 micrograms oligo-dT primer (P-L Bio-chemicals) or 1 micrograms synthetic primer, 28 units placental ribonuclease inhibitor (Bethesda Research Labs #5518SA), 100 mM Tris pH 8.3, 140 mM KCl, 10 mM MgCl$_2$, 0.8 mM DATP, dCTP, dGTP, and dTTP (Pharmacia), 100 microcuries $^{32}$P-labeled dCTP (New England Nuclear #NEG-013H), and 180 units AMV reverse transcriptase (Molecular Genetics Resources #MG 101). The reaction was incubated at 42° C. for 90 min, and then was terminated with 20 mM EDTA pH 8.0. The sample was extracted with an equal volume of phenol/chloroform (1:1) and precipitated with 2M ammonium acetate and 2 volumes of cold ethanol −20° C. for 3 hrs. After precipitation and centrifugation, the pellet was dissolved in 100 microliters distilled water. The sample was loaded onto a 15 ml G-100 Sephadex column (Pharmacia) in buffer (100 mM Tris pH 7.5, 1 mM EDTA pH 8.0, 100 mM NaCl). The leading edge of the eluted DNA fractions was pooled, and DNA was concentrated by lyophilization until the volume was about 100 microliters, then the DNA was precipitated with ammonium acetate plus ethanol as above.

The entire first strand sample was used for second strand reaction which followed the Gubler and Hoffman (supra) method except that 50 micrograms/ml dNTP's, 5.4 units DNA polymerase I (Boerhinger Mannheim #642–711), and 100 units/ml *E. coli* DNA ligase (New England Biolabs #205) in a total volume of 50 microliters were used. After second strand synthesis, the cDNA was phenol/chloroform extracted and precipitated. The DNA was resuspended in 10 microliters distilled water, treated with 1 micrograms RNase A for 10 min at 22° C., and electrophoresed through a it agarose gel (sigma Type II agarose) in 40 mM Tris-acetate pH 6.85. The gel was stained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 microliters water.

Oligo-dC tails were added to the DNA to facilitate cloning. The reaction contained the DNA, 100 mM potassium cacodylate pH 7.2, 0.2 mM dithiothreitol, 2 mM $CaCl_2$, 80 micromoles dCTP, and 25 units terminal deoxynucleotidyl transferase (Molecular Genetic Resources #S1001) in 50 microliters. After 30 min at 37° C., the reaction was terminated with 10 mM EDTA, and the sample was phenol/chloroform extracted and precipitated as above.

The dC-tailed DNA sample was annealed to 200 ng plasmid vector pBR322 that contained oligo-dG tails (Bethesda Research Labs #5355 SA/SB) in 200 microliters of 0.01M Tris pH 7.5, 0.1M NaCl, 1 mM EDTA pH 8.0 at 65° C. for 2 min and then 57° C. for 2 hrs. Fresh competent *E. coli* DH-1 cells were prepared and transformed as described by D. Hanahan, *Molecular Biology* 166, 557–580, 1983, using half the annealed cDNA sample in twenty 200 microliters aliquots of cells. Transformed cells were plated on L-broth agar plates plus 10 micrograms/ml tetracycline. Colonies were screened for the presence of inserts into the ampicillin gene using Ampscreen (Bethesda Research Labs #5537 UA), and the positive colonies were picked for analysis.

Example 10

DNA Transfection For Generating Recombinant Marek's Disease Virus

The method is based upon the polybrene-DMSO procedure of Kawai and Nishizawa, Mol. and Cell. Biol. 4:1172–1174 (1984) with the following modifications. Generation of recombinant MDV virus is dependent upon homologous recombination between MDV viral DNA and the plasmid homology vector containing the desired foreign DNA flanked by the appropriate herpesvirus cloned sequences. Transfections were carried out in 6 cm plates (Corning plastic) of 50% confluent primary chick embryo fibroblast (CEF) cells. The cells were plated out the day before in CEF growth media (1×F10/199, 5% fetal calf serum, 2% glutamine, 1% non-essential amino acids, and 2% penicillin/streptomycin) containing 4 microgratns/ml polybrene (stock 4 mg/ml in 1×HBSS). For cotransfections into CEF cells, 5 micrograms of intact MDV DNA, and suspended in 1 ml of CEF media containing 30 micrograms/ml polybrene (stock 4 mg/ml in 1×HBSS). The DNA-polybrene suspension (1 ml) was then added to a 6 cm plate of CEF cells from which the media had been aspirated, and incubated at 39° C. for 30 minutes. The plates were rocked periodically during this time to redistribute the inoculum. After this period, 4 ml of CEF growth media was added directly to wash plate, and incubated an additional 2.5 hours at 39° C. At this time, the media was removed from each plate, and the cells shocked with 2 ml of 30% DMSO (Dimethyl Sulfoxide, J. T. Baker Chemical Co., Phillipsburg, N.J.) in 1×HBSS for 4 minutes at room temperature. The 30% DMSO was carefully removed and the monolayers washed once with 1×HBSS at room temperature. The cells were then incubated at 39° C. after the addition of 5 mls of CEF growth media. The next day, the media was changed to remove any last traces of DMSO and to stimulate cell growth. Cytopathic effect from the virus becomes apparent within 6 days. Generation of a high titer stock (80%–90% CPE) can usually be made within 1 week from this date. MDV stock samples were prepared by resuspending the infected cells in CEF growth media containing 20% fetal calf serum, 10% DMSO and stored at −70° C.

Example 11

Screen For Recombinant Marek's Disease Virus Expressing β-Galactosidase (Bluogal And CPRG Assays) Or β-Glucuronidase (X-Gluc Assay)

When the *E. coli* β-galactosidase (lacZ) marker gene was incorporated into a recombinant virus the plaques containing the recombinants were visualized by one of two simple methods. In the first method, the chemical Bluogal™ (Life Sciences Technology, Bethesda, Md.) was incorporated (200 μg/ml) into the agarose overlay during the plaque assay, and plaques expressing active β-galactosidase turned blue. The blue plaques were then picked onto fresh CEF cells and purified by further blue plaque isolation. In the second method, CPRG (Boehringer Mannheim) was incorporated (400 μg/ml) into the agarose overlay during the plaque assay, and plaques expressing active β-galactosidase turned red. The red plaques were then picked onto fresh cells CEF cells and purified by further red plaque isolation. In both cases viruses were typically purified with three to four rounds of plaque purification.

When the *E. coli* β-glucuronidase (uidA) marker gene was incorporated into a recombinant virus the plaques containing the recombinants were visualized by using the chromogenic substrate, X-β-D-gluUA CHX (X-GLUC; 5-Bromo-4-chloro-3-indoxyl-β-D-glucuronic acid, cyclohexylammonium salt; Biosynth AG; Switzerland) was incorporated (200 μg/ml) into the agarose overlay during the plaque assay, and plaques expressing active β-glucuronidase turned blue. The blue plaques were then picked onto fresh CEF cells and purified by further blue plaque isolation.

Example 12

Screen For Foreign DNA sequence Expression In Recombinant Marek's Disease Virus Using Black Plaque Assays To analyze expression of foreign antigens expressed by recombinant MDV viruses, monolayers of CEF cells are infected with recombinant MDV, overlaid with nutrient agarose media and incubated for 4–5 days at 39° C. Once plaques have developed, the agarose overlay is removed from the dish, the monolayer rinsed 1× with PBS, fixed with 100% methanol for 10 minutes at room temperature and the cells air dried. After re-hydrating the plate with PBS, the primary antibody is diluted to the appropriate dilution with PBS and incubated with the cell monolayer for 2 hours to overnight at room temperature. Unbound antibody is then removed from the cells by washing three times with PBS at room temperature. An alkaline phosphatase conjugated secondary antibody is diluted with PBS and incubated with the cells for 2 hours at room temperature. Unbound secondary antibody is then removed by washing the cells three times with PBS at room temperature. Next, the monolayer is rinsed in color development buffer (100 mM Tris pH 9.5/100 mM NaCl/5 mM MgCl2), and then incubated 10 minutes to overnight at room temperature with freshly prepared substrate solution (0.3 mg/ml Nitro Blue tetrazolium+0.15 mg/ml 5-Bromo-4-Chloro-3-Indolyl Phosphatase in color development buffer.) Finally, the reaction is stopped by replacing the substrate solution with TE (10 mM Tris, pH7.5/1 mM EDTA). Plaques expressing the correct antigen will stain black.

Example 13

Plasmid Having Foreign DNA Inserted Into Open Reading Frame UL54.5 of Marek's Disease Virus Type 1

The plasmid 440–29.2 was constructed for the purpose of inserting foreign DNA into Marek's disease virus type 1

(MDV-1). It comprises the approximately 2596 base pair Bam HI "M" genomic fragment of Marek's disease virus type 1 (SEQ ID NO. 1). Three open reading frames within the Bam HI "M" fragment are the herpesvirus homologs of the UL54 (ICP27) ORF (Position 1 to 1353 of SEQ ID NO. 1), a previously unidentified ORF hence named UL54.5 (Position 2187 to 1483 of SEQ ID NO. 1) and UL55 (Position 2459 to 2593 of SEQ ID NO. 1) (see FIGS. 1 and 2). DNA sequence (1492 base pairs) spanning the MDV-1 UL54 (ICP27) gene has been published (Virology 1994 October; 204(1):242–50). MDV ICP27, based on significant similarity to HSV-1 ICP27, is 1419 nucleotides long and encodes 473 amino acids (54.5 kDa). The UL55 ORF is truncated and contained only the first 49 amino acids of this protein. A potential ORF located between UL54 and UL55 was identified. This ORF is 705 base pairs long and potentially encodes a protein of 235 amino acids in size. BLAST searches of protein data bases using the UL54.5 amino acid sequence identified a similar gene in MDV-2 (Virology 1994 May 15;201(1):142–6). It was noted that the MDV-2 gene shared low homology with the equine herpes virus type 1 the first open reading frame (ORF-1). The similarity index of the UL54.5 proteins from MDV-1 and MDV-2 is 63 percent over a consensus length of 170 amino acids. UL54.5 is transcribed in the opposite orientation relative to UL54 and UL55.

The UL54.5 ORF is non-essential and foreign DNA is inserted within this ORFs or in the intergenic region between the ORFs. Any restriction site within this region is useful as an insertion site for foreign DNA. A restriction enzyme site within this region which is not unique is altered by insertion of a DNA linker which converts the site to a unique restriction enzyme recognition sequence. Preferably the restriction enzyme site used for insertion of foreign DNA is an Nde I site at approximately nucleotide 2173 within the 2596 base pair Bam HI "M" genomic fragment. The insertion site is within the UL54.5 ORF between amino acids 4 and 5 of the open reading frame. The plasmid vector was derived from an approximately 3045 base pair Bam HI restriction fragment of pSP64 (Promega). Fragment 1 is an approximately 2596 base pair Bam HI "M" genomic fragment of Marek's disease virus type 1. Plasmid 440–29.2 was used to make homology vectors for insertion of foreign DNA in recombinant Marek's disease virus.

Example 14

Plasmid Having Infectious Laryngotracheitis Virus DNA Inserted Into Open Reading Frame UL54.5 of Marek's Disease Virus Type 1

The plasmid 980-85.01 was constructed for the purpose of inserting foreign DNA into recombinant Marek's disease virus type 1 (MDV-1). It incorporates the ILT virus gD and gI genes and the *E. coli* β-galactosidase (lacZ) marker gene flanked by MDV-1 DNA. These genes were inserted into a unique Nde I site converted to a Pac I site using synthetic DNA linkers. Upstream of the foreign DNA sequence is an approximately 422 base pair fragment of MDV DNA. Downstream of the foreign DNA sequences is an approximately 2174 base pair fragment of MDV DNA. Direction of transcription of the ILT virus gD and gI genes and the *E. coli* β-galactosidase (lacZ) marker gene is opposite the direction of transcription of the MDV UL54 and UL55 ORFs. When the plasmid is used according to the DNA Transfection For Generating Recombinant Marek's Disease Virus 11) and Screen For Recombinant Marek's Disease Virus Expressing β-Galactosidase (Bluogal And CPRG Assays) Or β-Glucuronidase (X-Gluc Assay), (Example 11), a virus containing DNA coding for the foreign DNA sequences will result. The ILTV gD and gI genes are expressed as overlapping transcripts from their own respective endogenous ILTV promoters, and share their own endogenous polyadenylation signal, and the *E. coli* β-galactosidase (lacZ) marker gene is transcribed from the PRV gX promoter and is followed by the PRV gX poly adenylation signal.

Plasmid 980-85.1 was constructed utilizing standard recombinant DNA techniques by joining restriction fragments from the following sources with the synthetic DNA sequences. The ILT gD, gI, and the *E. coli* β-galactosidase (lacZ) marker gene was inserted as a cassette into the homology vector 440-29.2 at the unique Nde I site which was converted to a Pac I site using synthetic DNA linkers. The plasmid vector was derived from an approximately 3045 base pair Hind III restriction fragment of pSP64 (Promega). Fragment 1 is an approximately 418 base pair Bam HI to Nde I restriction sub-fragment of the MDV Bam HI restriction fragment M. Fragment 2 is an approximately 3556 base pair Sal I to Hind III restriction subfragment of the ILTAsp718I genomic fragment #8 (10.6 kilobases). Fragment 3 is an approximately 413 base pair Sal I to Bam HI restriction subfragment of the PRV Bam HI restriction fragment #10. Fragment 4 is an approximately 3010 base pair Bam HI to Pvu II restriction fragment of plasmid pJF751 (11). Fragment 5 is an approximately 754 base pair Nde I to Sal I restriction subfragment of the PRV Bam HI restriction fragment #7. Fragment 6 is an approximately 2174 base pair Nde I to Bam HI restriction sub-fragment of the MDV Bam HI restriction fragment M.

Example 15

Plasmid Having Newcastle Disease Virus DNA Inserted Into Open Reading Frame UL54.5 of Marek's Disease Virus Type 1

The plasmid 980-46.74 was constructed for the purpose of inserting foreign DNA into recombinant Marek's disease virus Type 1 (MDV-1). It incorporates an *E. coli* β-galactosidase (lacZ) marker gene and Newcastle disease virus (NDV) F gene flanked by MDV DNA. The *E. coli* β-galactosidase (lacZ) marker gene and NDV F gene were inserted as a cassette into the homology vector 440-29.2 (Example 13) into the unique Nde I site converted to a Pac I site using synthetic DNA linkers.

Upstream of the foreign DNA sequences is an approximately 422 base pair fragment of MDV DNA. Downstream of the foreign DNA sequences is an approximately 2174 base pair fragment of MDV DNA. Direction of transcription of the *E. coli* β-galactosidase (lacZ) marker gene and the NDV F gene is opposite the direction of transcription of the MDV UL54 and UL55 ORFs. When the plasmid is used according to the DNA Transfection For Generating Recombinant Marek's Disease Virus (Example 10) and Screen For Recombinant Marek's Disease Virus Expressing β-Galactosidase (Bluogal And CPRG Assays) Or β-Glucuronidase (X-Gluc Assay), (Example 11), a virus containing DNA coding for the foreign DNA sequences will result. The NDV F gene is under the control of the HCMV immediate early promoter and is followed by the HSV TK poly adenylation signal. The *E. coli* β-galactosidase (lacZ) marker gene is transcribed from the PRV gX promoter and is followed by the PRV gX poly adenylation signal.

Plasmid 980-85.1 was constructed utilizing standard recombinant DNA techniques by joining restriction fragments from the following sources with the synthetic DNA sequences. The E. coli β-galactosidase (lacZ) marker gene and the NDV F gene were inserted as a cassette into the homology vector 440-29.2 (Example 13) at the unique Nde I site which was converted to a Pac I site using synthetic DNA linkers. The plasmid vector was derived from an approximately 3045 base pair Hind III restriction fragment of pSP64 (Promega). Fragment 1 is an approximately 418 base pair Bam HI to Nde I restriction sub-fragment of the MDV Bam HI restriction fragment M. Fragment 2 is an approximately 413 base pair Sal I to Bam HI restriction subfragment of the PRV Bam HI restriction fragment #10. Fragment 3 is an approximately 3010 base pair Bam HI to Pvu II restriction fragment of plasmid pJF75 1. Fragment 4 is an approximately 754 base pair Nde I to Sal I restriction subfragment of the PRV Bam HI restriction fragment #7. Fragment 5 is an approximately 1191 base pair Pst I to Ava II restriction subfragment of the HCMV genomic Xba I E fragment. Fragment 6 is an approximately 1812 base pair Bam HI to Pst I restriction fragment of the full length NDV F cDNA clone (B1 strain). Fragment 7 is an approximately 784 base pair Sma I to Sma I restriction subfragment of the HSV Bam HI restriction fragment Q. The last fragment is an approximately 2174 base pair Nde I to Bam HI restriction sub-fragment of the MDV Bam HI restriction fragment "M".

Example 16

Plasmid Having Foreign DNA Inserted Into Open Reading Frame UL43 of Marek's Disease Virus Type 1

Figure 3:
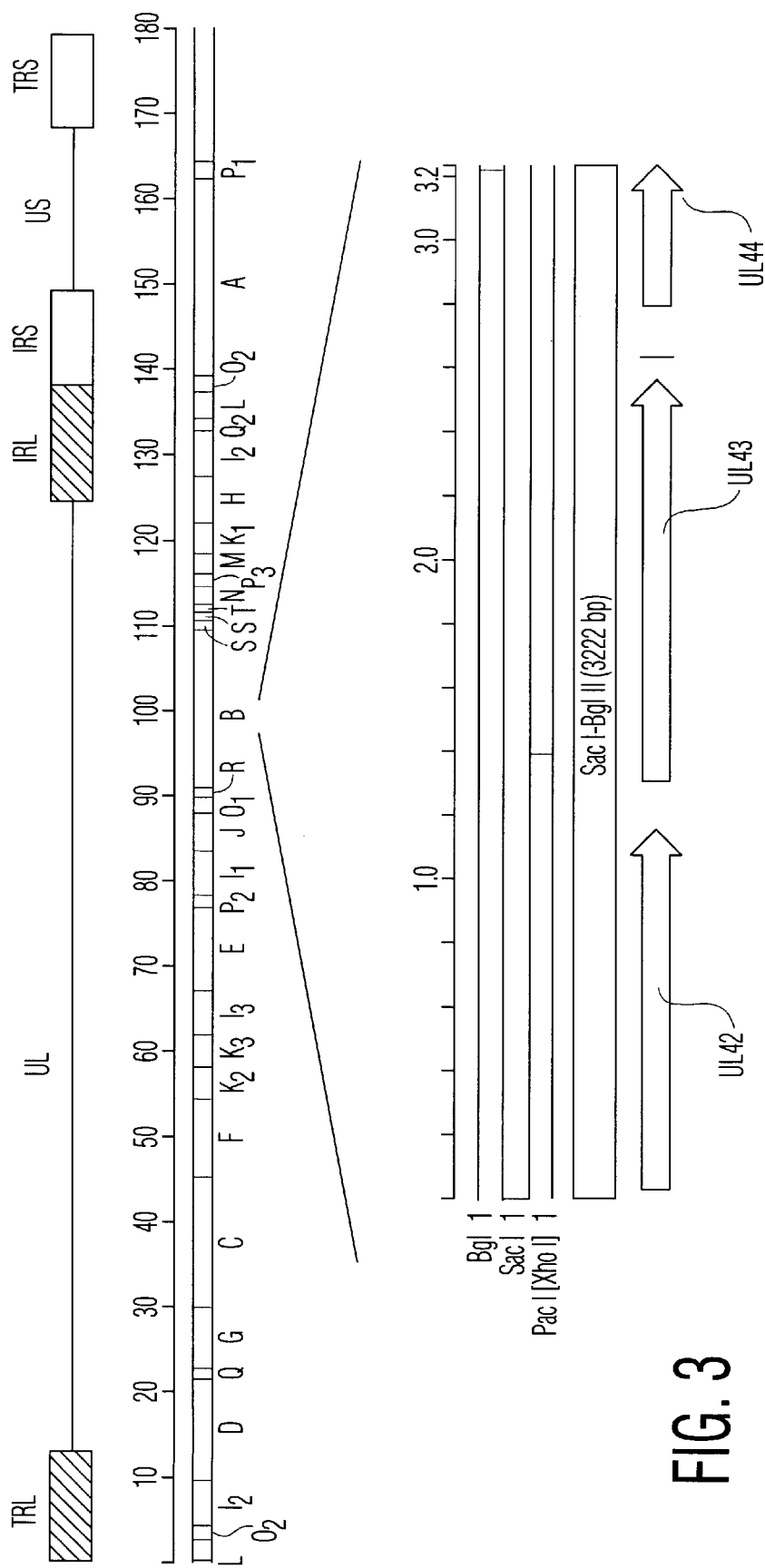
FIG. 3 is a BamH1 restriction map of an MDV genome particularly pointing out the location of ScdI-BglIII fragments.
Figure 4:
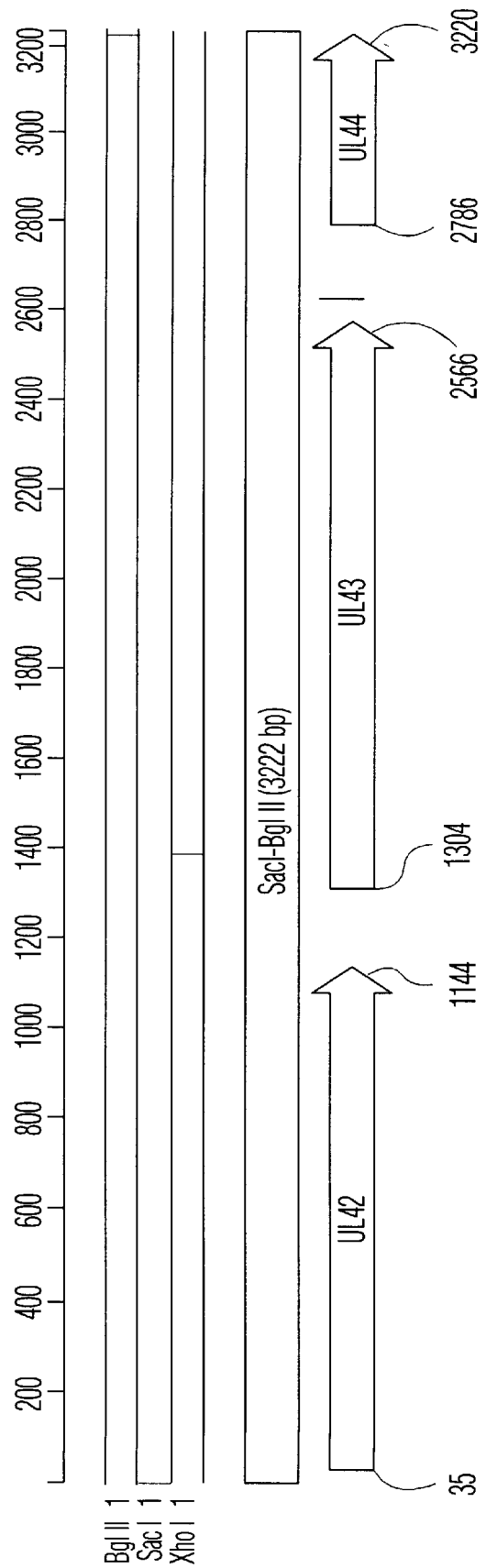
FIG. 4 is a map designating the open reading frames in the SacI-BalIII fragment of an MDV genome.

The plasmid 962-80.1 was constructed for the purpose of inserting foreign DNA into Marek's disease virus type 1 (MDV-1). It comprises the approximately 3212 base pair Sac I to Bgl II subfragment contained within the Bam HI "B" genomic fragment of Marek's disease virus type 1 (SEQ ID NO. 2). Three open reading frames within the 3212 base pair Sac I to Bgl II subfragment are the herpesvirus homologs of the UL42 ORF (Position 35 to 1144 of Seq ID No. 2), UL43 (Position 1304 to 2566 of Seq ID No. 2) and UL44 (gC) (Position 2786 to 3220 of Seq ID No. 2) (see FIGS. 3 and 4). DNA sequence (732 base pairs) spanning the MDV-1 UL44 (gC) gene and promoter region have been published (Virus Genes 3, 125–137 (1989)). DNA sequence of MDV-2 UL42, UL43, and UL44 genes have been published (J. Gen. Virol. 79 (Pt 8), 1997–2001 (1998). The similarity index of the UL42 proteins from MDV-1 and MDV-2 is 74 percent over a consensus length of 369 amino acids. The similarity index of the UL43 proteins from MDV-1 and MDV-2 is 54 percent over a consensus length of 401 amino acids. The similarity index of the UL44 proteins from MDV-1 and MDV-2 is 45 percent over a consensus length of 145 amino acids. The MDV-1 UL43 ORF is non-essential and foreign DNA is inserted within this ORFs or in the intergenic region between the ORFs. Any restriction site within this region is useful as an insertion site for foreign DNA. A restriction enzyme site within this region which is not unique is altered by insertion of a DNA linker which converts the site to a unique restriction enzyme recognition sequence. Preferably the restriction enzyme site used for insertion of foreign DNA is an Xho I site at approximately nucleotide 1386 within the 3212 base pair Sac I to Bgl II subfragment contained within the Bam HI "B" genomic fragment of Marek's disease virus type 1. The insertion site is within the UL43 ORF between amino acids 29 and 30 of the open reading frame. The plasmid vector was derived from an approximately 3045 base pair Bam HI restriction fragment of pSP64 (Promega). Fragment 1 is an approximately 3212 base pair Sac I to Bgl II subfragment contained within the Bam HI "B" genomic fragment of Marek's disease virus type 1. Plasmid 962-80.1 was used to make homology vectors for insertion of foreign DNA in recombinant Marek's disease virus.

Example 17

Plasmid Having Infectious Laryngotracheitis Virus DNA Inserted Into Open Reading Frame UL43 of Marek's Disease Virus Type 1

The plasmid 980-85.22 was constructed for the purpose of inserting foreign DNA into recombinant Marek's disease virus type 1 (MDV-1). It incorporates the ILT virus gD and gI genes and the E. coli β-galactosidase (lacZ) marker gene flanked by MDV-1 DNA. These genes were inserted into a unique Xho I site converted to a Pac I site using synthetic DNA linkers. Upstream of the foreign DNA sequence is an approximately 1386 base pair fragment of MDV DNA. Downstream of the foreign DNA sequences is an approximately 1826 base pair fragment of MDV DNA. Direction of transcription of the ILT virus gD and gI genes and the E. coli β-galactosidase (lacZ) marker gene is the same direction of transcription as the MDV UL42 and UL43 ORFs. When the plasmid is used according to the DNA Transfection For Generating Recombinant Marek's Disease Virus (Example 10) and Screen For Recombinant Marek's Disease Virus Expressing β-Galactosidase (Bluogal And Cprg Assays) Or β-Glucuronidase (X-Gluc Assay), (Example 11) a virus containing DNA coding for the foreign DNA sequences will result. The ILTV gD and gI genes are expressed as overlapping transcripts from their own respective endogenous ILTV promoters, and share their own endogenous polyadenylation signal, and the E. coli β-galactosidase (lacZ) marker gene is transcribed from the PRV gX promoter and is followed by the PRV gX poly adenylation signal.

Plasmid 980-85.22 was constructed utilizing standard recombinant DNA techniques by joining restriction fragments from the following sources with the synthetic DNA sequences. The ILT gD, gI, and the E. coli β-galactosidase (lacZ) marker gene was inserted as a cassette into the homology vector 962-80.1 at the unique Xho I site which was converted to a Pac I site using synthetic DNA linkers. The plasmid vector was derived from an approximately 3045 base pair Hind III restriction fragment of pSP64 (Promega, Madison, Wis.). Fragment 1 is an approximately 1386 base pair Sac I to Xho I restriction subfragment contained within the Bam HI "B" genomic fragment of Marek's disease virus type 1. Fragment 2 is an approximately 3556 base pair Sal I to Hind III restriction subfragment of the ILTAsp718I genomic fragment #8 (10.6 kilobases). Fragment 3 is an approximately 413 base pair Sal I to Bam HI restriction subfragment of the PRV Bam HI restriction fragment #10. Fragment 4 is an approximately 3010 base pair Bam HI to Pvu II restriction fragment of plasmid pJF751 (11). Fragment 5 is an approximately 754 base pair Nde I to Sal I restriction subfragment of the PRV Bam HI restriction fragment #7. Fragment 6 is an approximately 1826 base pair Xho I to Bgl II restriction subfragment contained within the Bam HI "B" genomic fragment of Marek's disease virus type 1.

Example 18

Recombinant Marek's Disease Virus Type 1 Having Infectious Laryngotracheitis Virus DNA Inserted Into Open Reading Frame UL43

S-MDV-006 is a Marek's disease type 1 virus that expresses three foreign DNA sequences. The genes for ILT virus gD and gI and the E. coli β-galactosidase (lacZ) marker gene were inserted into a unique Pac I restriction site (Pac I linkers inserted into a unique Xho I restriction site in the UL43 ORF of the approximately 3212 base pair Sac I to Bgl II subfragment contained within the Bam HI "B" genomic fragment of Marek's disease virus type 1. The ILTV gD and gI genes are expressed as overlapping transcripts from their own respective endogenous ILTV promoters, and share their own endogenous polyadenylation signal, and the E. coli β-galactosidase (lacZ) marker gene is transcribed from the PRV gX promoter and is followed by the PRV gX poly adenylation signal. S-MDV-006 was derived from S-MDV-002 (MDV-1; CVI-988 Rispens). This was accomplished utilizing the homology vector 980-85.22 and virus S-MDV-002 in the DNA Transfection For Generating Recombinant Marek's Disease Virus procedure (Example 10). The co-transfection stock was screened by the B-Glucuronidase (X-Gluc Assay) (Example 11). The final result of red plaque purification was the recombinant virus designated S-MDV-006. This virus was assayed for β-galactosidase expression, purity, and insert stability by multiple passages monitored by the blue plaque assay as described in Example 11. After the initial four rounds of purification, all plaques observed are blue indicating that the virus is pure, stable, and expressing the foreign DNA sequences.

S-MDV-006 was assayed for expression of ILT specific antigens using the Screen For Foreign DNA Sequence Expression In Recombinant Marek's Disease Virus Using Black Plaque Assays (Example 12). Polyclonal chicken anti-ILT serum (SPAFAS) was shown to react specifically with S-MDV-006 plaques and not with S-MDV-002 negative control plaques. All S-MDV-006 observed plaques reacted with the polyclonal serum indicating that the virus was stably expressing the ILT foreign DNA sequences. The assay described here were carried out in CEF cells, indicating that CEF cells would be a suitable substrate for the production of MDV recombinant vaccines.

S-MDV-006 is a recombinant Marek's disease type 1 virus expressing the ILT gD and gI proteins and is useful as a vaccine in ILT infection. S-MDV-006 is also useful for expression of the ILT gD and gI proteins.

Example 19

Plasmid Having Newcastle Disease Virus DNA Inserted Into Open Reading Frame UL43 of Marek's Disease Virus Type 1

The plasmid 980-60.02 was constructed for the purpose of inserting foreign DNA into recombinant Marek's disease virus Type 1 (MDV-1). It incorporates an E. coli β-galactosidase (lacZ) marker gene and Newcastle disease virus (NDV) F gene flanked by MDV DNA. The E. coli β-galactosidase (lacZ) marker gene and NDV F gene were inserted as a cassette into the homology vector 962-80.1 into the unique Xho I site converted to a Pac I site using synthetic DNA linkers.

Upstream of the foreign DNA sequence is an approximately 1386 base pair fragment of MDV DNA. Downstream of the foreign DNA sequences is an approximately 1826 base pair fragment of MDV DNA. Direction of transcription of the E. coli β-galactosidase (lacZ) marker gene and the NDV F gene is the same direction of transcription as the MDV UL42 and UL43 ORFs. When the plasmid is used according to the DNA Transfection For Generating Recombinant Marek's Disease Virus (Example 10) and Screen For Recombinant Marek's Disease Virus Expressing β-Galactosidase (Bluogal And Cprg Assays) Or β-Glucuronidase (X-Gluc Assay), (Example 11), a virus containing DNA coding for the foreign DNA sequences will result. The NDV F gene is under the control of the HCMV immediate early promoter and is followed by the HSV TK poly adenylation signal. The E. coli β-galactosidase (lacZ) marker gene is transcribed from the PRV gX promoter and is followed by the PRV gX poly adenylation signal.

Plasmid 980-85.1 was constructed utilizing standard recombinant DNA techniques by joining restriction fragments from the following sources with the synthetic DNA sequences. The E. coli β-galactosidase (lacZ) marker gene and the NDV F gene were inserted as a cassette into the homology vector 962-80.1 at the unique Xho I site which was converted to a Pac I site using synthetic DNA linkers. The plasmid vector was derived from an approximately 3045 base pair Hind III restriction fragment of pSP64 (Promega).

Fragment 1 is an approximately 1386 base pair Sac I to Xho I restriction subfragment contained within the Bam HI "B" genomic fragment of Marek's disease virus type 1.

Fragment 2 is an approximately 413 base pair Sal I to Bam HI restriction subfragment of the PRV Bam HI restriction fragment #10. Fragment 3 is an approximately 3010 base pair Bam HI to Pvu II restriction fragment of plasmid pJF751. Fragment 4 is an approximately 754 base pair Nde I to Sal I restriction subfragment of the PRV Bam HI restriction fragment #7. Fragment 5 is an approximately 1191 base pair Pst I to Ava II restriction subfragment of the HCMV genomic Xba I E fragment. Fragment 6 is an approximately 1812 base pair Bam HI to Pst I restriction fragment of the full length NDV F cDNA clone (B1 strain). Fragment 7 is an approximately 784 base pair Sma I to Sma I restriction subfragment of the HSV Bam HI restriction fragment Q. The last fragment is an approximately 1826 base pair Xho I to Bgl II restriction subfragment contained within the Bam HI "B" genomic fragment of Marek's disease virus type 1.

Example 20

Recombinant Marek's Disease Virus Type 1 Having Newcastle Disease Virus DNA Inserted Into Open Reading Frame UL43

S-MDV-004 is a Marek's disease type 1 virus that expresses two foreign DNA sequences. The gene for Newcastle disease virus Fusion (F) and the E. coli β-galactosidase (lacZ) marker gene are inserted into a unique Pac I restriction site (Pac I linkers inserted into a unique Xho I restriction site in the UL43 ORF of the approximately 3212 base pair Sac I to Bgl II subfragment contained within the Bam HI "B" genomic fragment of Marek's disease virus type 1. The NDV F gene is under the control of the HCMV immediate early promoter, and the E. coli β-galactosidase (lacZ) marker gene is transcribed from the PRV gX promoter and is followed by the PRV gX poly adenylation signal. S-MDV-004 is derived from S-MDV-002 (MDV-1; CVI-988 Rispens). This is accomplished utilizing the homology vector 980-60.02 and virus S-MDV-002 in the DNA Transfection For Generating Recombinant Marek's Disease Virus (Example 10). The co-transfection stock was screened by the Screen For Recombinant Marek's Disease Virus Expressing β-Galactosidase (Bluogal And Cprg Assays) Or β-Glucuronidase (X-Gluc Assay), (Example 11). The final result of red plaque purification is the recombinant virus designated S-MDV-004. This virus is assayed for β-galactosidase expression, purity, and insert stability by multiple passages monitored by the blue plaque assay as described in Example 11. After the initial four rounds of purification, all plaques observed are blue indicating that the virus is pure, stable, and expressing the foreign DNA sequences.

S-MDV-004 is assayed for expression of NDV specific antigens using the Screen For Foreign DNA Sequence Expression In Recombinant Marek's Disease Virus Using Black Plaque Assays (Example 12). A monoclonal antibody specific for NDV F is shown to react specifically with S-MDV-004 plaques and not with S-MDV-002 negative control plaques. All S-MDV-004 observed plaques react with the polyclonal serum, indicating that the virus is stably expressing the NDV F gene. The assay described here is carried out in CEF cells, indicating that CEF cells would be a suitable substrate for the production of MDV recombinant vaccines.

S-MDV-004 is a recombinant Marek's disease type 1 virus expressing the NDV F protein and is useful as a vaccine in NDV infection. S-MDV-004 is also useful for expression of F protein.

Example 21
Plasmid Having Foreign DNA Inserted Into Open Reading Frame UL7 And/Or Between Open Reading Frames UL8 and UL7 of Marek's Disease Virus Type 1

Figure 5:
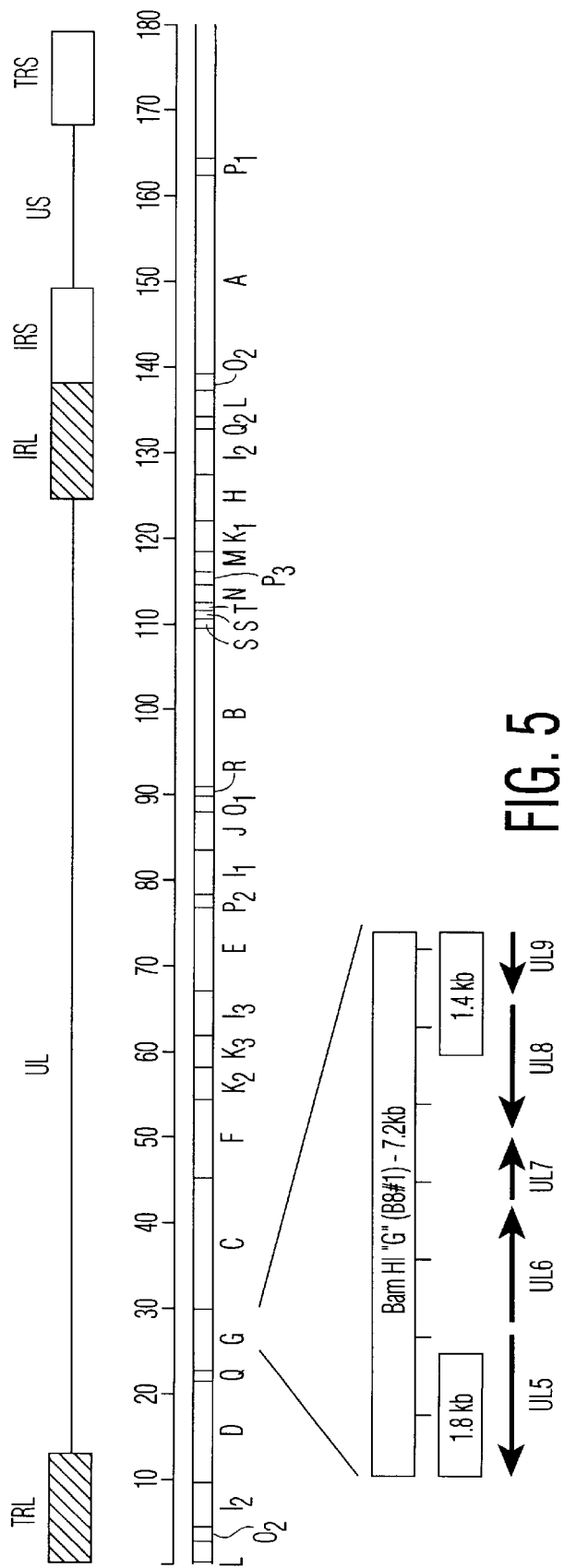
FIG. 5 is a BamH1 restriction map of an MDV genome particularly pointing out the location of a "G" fragment.
Figure 6:
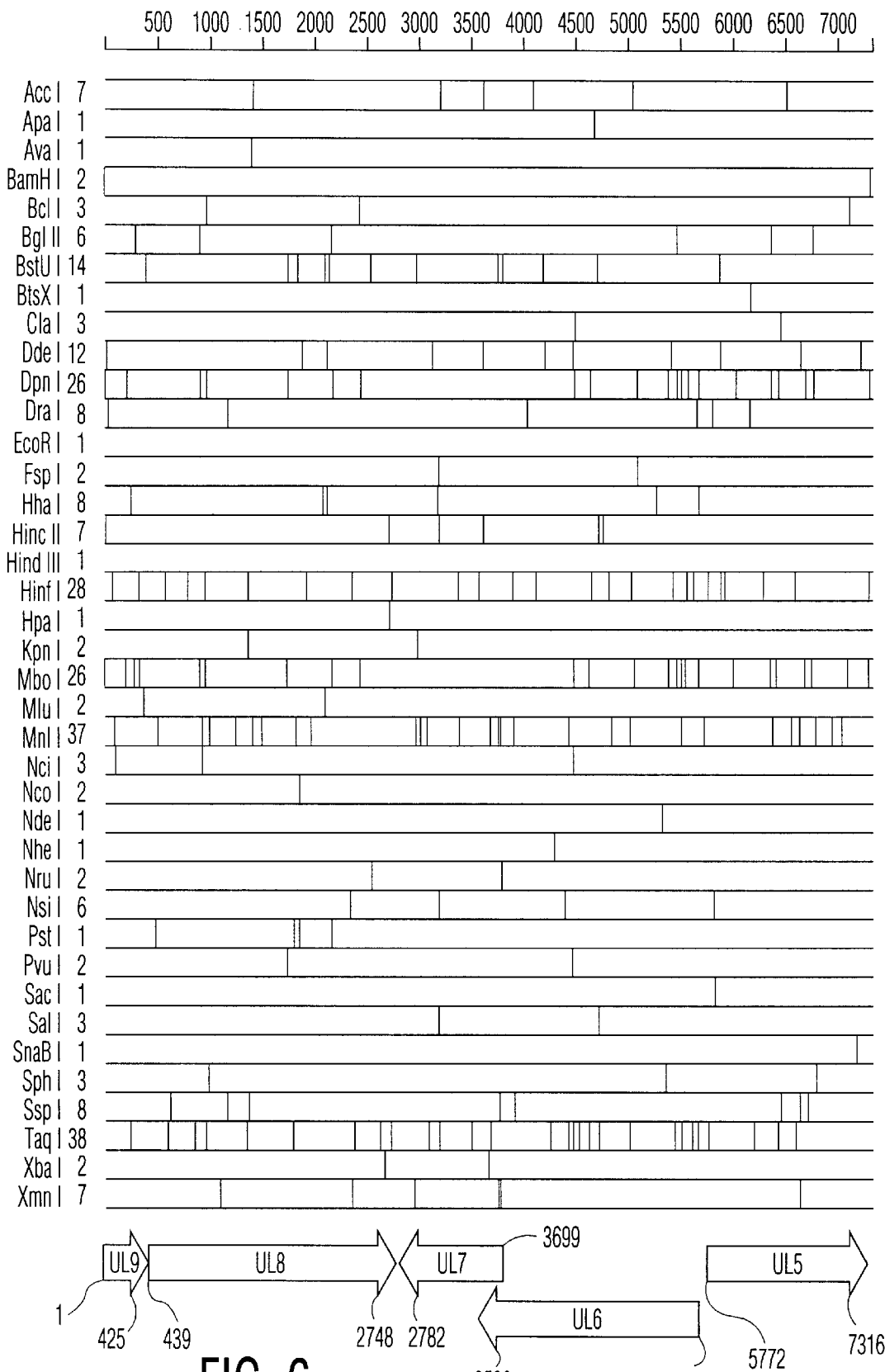
FIG. 6 is a map of the open reading frames in the BamHI "G" fragment of an MDV genome.

A plasmid is constructed for the purpose of inserting foreign DNA into Marek's disease virus type 1 (MDV-1). It comprises the approximately 7316 base pair subfragment contained within the Bam HI "G" genomic fragment of Marek's disease virus type 1 (SEQ ID NO. 3). Five open reading frames within the 7316 base pair subfragment are the herpesvirus homologs of the UL9 ORF (Position 1 to 425 of Seq ID No. 3), UL8 (Position 439 to 2748 of Seq ID No. 3), UL7 (gC) (Position 3699 to 2782 of Seq ID No. 3), UL6 (Position 5704 to 3536 of Seq ID No. 3) and UL5 (Position 5772 to 7316 of Seq ID No. 3) (see FIGS. 5 and 6). The area between ORFs UL 8 and UL 7 Position 2749 to 2781 of Seq ID No. 3), and the portion of ORF 7 that does not overlap with ORF UL 6 (Position 2782 to 3535 of Seq ID No. 3) is nonessential to viral replication and can be used to create mutant and/or recombinant viruses.

From the above, it is clear that the present invention provides novel recombinant and mutant viruses and DNA deletion and/or insertion sites for the creation of new viral vectors.

What is claimed is:

1. A recombinant Marek's disease virus (MDV) comprising a foreign DNA sequence inserted into the UL54.5 open reading frame of the Marek's disease virus genome.

2. The recombinant virus of claim 1, wherein said foreign DNA encodes a polypeptide.

3. The recombinant virus of claim 2, wherein said polypeptide comprises more than ten amino acids.

4. The recombinant virus of claim 2, wherein said polypeptide is antigenic.

5. The recombinant virus of claim 1, wherein said foreign DNA sequence is under control of an active herpesvirus promoter located upstream of said foreign DNA sequence and is selected from the group consisting of PRV gX promoter, MDV gB promoter, MDV gA promoter, MDV gD promoter, ILTV gB promoter, ILTV gI promoter, HCMV immediate early promoter and substantially homologous sequences.

6. The recombinant virus of claim 1, wherein said foreign DNA sequence encodes an antigenic polypeptide from a virus selected from the group consisting of chicken anemia virus, infectious bursal disease, Marek's disease virus, Newcastle disease virus, infectious laryngotracheitis virus, infectious bronchitis virus, and substantially homologous sequences.

7. The recombinant virus of claim 6, wherein said foreign DNA sequence comprises a DNA sequence encoding an antigenic polypeptide from infectious bursal disease virus selected from the group consisting of VP2, VP3, VP4, and substantially homologous sequences.

8. The recombinant virus of claim 6, wherein said foreign DNA comprises a DNA sequence encoding an antigenic polypeptide from Marek's disease virus selected from the group consisting of glycoprotein B, glycoprotein D, glycoprotein A, and substantially homologous sequences.

9. The recombinant virus of claim 6, wherein said foreign DNA comprises a DNA sequence encoding an antigenic polypeptide from Newcastle's disease virus selected from the group consisting of F, HN and substantially homologous sequences.

10. The recombinant virus of claim 6, wherein said foreign DNA comprises a DNA sequence encoding an antigenic polypeptide from infectious bronchitis virus selected from the group consisting of spike protein, nucleocapsid protein, matrix protein and substantially homologous sequences.

11. A mutant Marek's disease virus (MDV) comprising a deletion of at least a portion of the UL54.5 open reading frame of the Marek's disesase virus genome.

12. The mutant virus of claim 11, wherein said UL54.5 open reading frame is completely deleted.

* * * * *

SEQUENCE LISTING

<160> NUMBER OF SEQ ID NOS: 3

<210> SEQ ID NO 1
<211> LENGTH: 2596
<212> TYPE: DNA
<213> ORGANISM: Marek's Disease Virus 1

<400> SEQUENCE: 1

```
ggatcctcct ccgatgaaaa tgccgaagtg actgaaatgg aaacatctgc aaaaacggct      60
aataacaaga atgaagtttt attcgcgcca ccgtgtacgc aggaactttt gaccgaacga     120
ccatctcctg attccaaaaa ttcgcaaggc gacgatgact caaattcaat atatggcaac     180
gtgattcgtg atgctcaaca ctcagcaagt cgatatgcta caaggtgtct tgacaatgca     240
ataccacgga aacgtctacg cttagctaat ttgacagtag attctgcatg catttcccaa     300
actaaacggc cgcacggtac aggcaatcgc aaacaatatc acagacgtaa ttttccgatg     360
tcaccgactt cacaagaaaa aattcatcta cgattgcaca accgacttgg atctcggagc     420
gaaaaacagc agcgcagtct aaattacgac cgacgtctgc aagaagggca tcaccgaaga     480
agattctaca gtgagacg tatttatgat caaaatcata gtcaccatcg tacacacgat      540
atacgggtac cattggaaaa atatagagtt tccagacaac atgatctccc tgtccatgag     600
gaactaaacg aaatacttca aagagagaaa caccgtctgg cctctatttc aaatgagtgt     660
gattttcgcg tttcgagcaa aaatcgatgg gctgccgtat taacattttc aagcaacgcg     720
gagagtacct tatgtggtcc tcagataaca tgggagtatt tattgcatgc gggtccagag     780
ctacgaaaca cgttcgaaat cagacctaga atatcgctac aagcaagtgc agcacgagaa     840
gccgtgttgc gaggtgaaag tttcattgcc gcattaggga gtgctgaaga aactctgtcg     900
tggttaaaac tacatgctgt tttaaagtta cgcctagtaa atcatgaccc gatttttaag     960
accgctggtg cggttttaga taacctcagg ctgaagctcg caccaataat gatgtgtaaa    1020
tatggaacag agaaacgctc catgggggat atgttaagaa gatctgctcc tgaagatata    1080
aacgattcct taactctgtg cttaattttg ttatcgcgca ttcgtcgtgt gatgcatcgc    1140
```

-continued

```
acatcgggca gcaaatacag ttatatgata gaccctagag gatgtatgat agactatgta   1200
cctggagaat gtatgacaaa tatactacgt tatgtagatg cgcatacgag gagatgttct   1260
gatcccgcat gtaacttgta tatcagctgc acactcatgc ctatttatat ccatggcagg   1320
tatttttact gcaatactct gtttggtatg taaatagtta tctaaaagac atcctatatt   1380
tagtattcta cacaatttct tctgacgata ttactaactc ctctaataaa gttaaataaa   1440
taaacgtctc agatatgtct tgttaaagtg tggttttatt atctatatat caccgacttt   1500
agatacggaa tatgaaaatg atggccctga aattgcacga acagctgtgg tgaagattcc   1560
gtcaaattta catttgaaat ttaagtatat aaattcaggt gatcctataa catcgttaaa   1620
caagctctcg agtagtttaa tgaacgctaa acattgaagt ccaccagggc gatcacaaag   1680
gcagttgact aacatgccat gcgctccagg attgtcgcga actgccgact cgcataaaca   1740
aataattttt ctcggatctc tcatttccag aaatctacgc gggtccatca gcaatgccgg   1800
ttttattcct ggaacacagt tagacgtaaa ctgctcgaaa actgttttaa gcacaaccgg   1860
gatgtctgca aaagccgatg atgcttcctt ataacagcgc tcagttagaa accataacag   1920
ttcttttggt agtatatttc ttcctagaaa ccatggcgtt cccatcgcta agaaccaagc   1980
atgtgttttc actgtatctt gtccaaagag ccctctattc ggagatgtat gttggagatc   2040
ggatgtccag agtactgctt tatctcgcat agatgaggtc gcagttacaa ttctcccttt   2100
ccagccaccc gtcaacatga tgtttattgg actaccaaca ttggtaatga gtactggtct   2160
ggcgactatt ccatatgcat tagtcattga aatttctcgt ggaatcagcc aaactggaga   2220
atctgcacat ctttattatt cgatgtggaa tgaccatgat cgctttgttg gtctgtaccg   2280
ttagcagaca tattcagagt aatgtcacga agacttaagg gtggctttca tttcaaacct   2340
ggagaacttg tagggttgta tagtcgacag gatgtaggtg gagacatgac gtctacaaag   2400
agacatccta taaggccatt cctgcagaaa cttataggtt tataccagag acgactcaat   2460
ggcagcaggg gcgatgtcat cgtcaacatt ggctcaaata ccgaatgtat accaagttat   2520
tgatccctta gcgattgata catcgtcgac atctacaaaa cgattactgg atgaacctgt   2580
accacacata ggatcc                                                   2596
```

<210> SEQ ID NO 2
<211> LENGTH: 3222
<212> TYPE: DNA
<213> ORGANISM: Marek's Disease Virus 1

<400> SEQUENCE: 2

```
gagctcctct aattccgata accggctgtt gtcaatggca ggaataacta tgggcagcga     60
acacatgtat gatgatacaa cgttcccaac aaacgatcct gagtcttcat ggaaaattgt    120
tttggctgga gagaaattta tgacagcatc ggctgcatta aaaacaatag taggttgcgt    180
gaagaaccca ttaattacat ttagcgacga cggactgatg atacagggca cggtttgcgg    240
tcaacgtatg tttgttccta tcgattgtac ttcattcagt gaatatgaat ggcgcgggcc    300
cacagcaata ttcctagctc ttaccgattc tagacgtacc ctcttagatg cattcaaatg    360
cgataagaaa aaagtagtag aagtttgttt tacctttcga ggagaaccac catgccgaca    420
tctaacacaa accgtcacat atgcaaatga tggatgctca ttttcgagta caatcgtcaa    480
atatgaatta tggagcgcat ccatcatttg tcctcaaaaa actccagatg ctacattttc    540
attaaacaaa caacaattga gcaaaattct aactgtagct gcaaaagtac aacatgaaga    600
```

-continued

| | |
|---|---|
| attgatctttt gctttgaaag ctgaaggagg tttttatgcc ggaacgattt gtgatgtgat | 660 |
| aagtttgat atagatggaa gcgcaatggt ccaatatccc tataatgcaa caagtcatgc | 720 |
| ttcgtcagcc ctcatcgtgg catgtgggaa gaaaaaaaca aataaaagta tagctgtaac | 780 |
| tgcatacggc agcgggaaac ctttctgcct tgcactggaa gatactaacg catttagaaa | 840 |
| tgtcgtgcaa aaaattaaaa cgggagccgc tggggcggat ttgggatttt atacaacgtg | 900 |
| tgatccaccg atgctgtgtg tacgtccgca cgtgtttgga agtcccacgg cattcctgtt | 960 |
| ttgcaattca gactgtatgt caatatacga attggaagaa gtgagtgcag tatctggagc | 1020 |
| aataaagtcg aaacgcatca gcggatattt ccccaaagta tcaaatatcg ctcccggaa | 1080 |
| acggggacca tcttcacccc ccttcgaacg agaagggaaa cttgccaaag ttatcaacca | 1140 |
| atgagacttt cgtgaggacc tgtaagtatg tcatggagtg ggagggttca tttatattgc | 1200 |
| atgtaagcct tatagaggat acaccagaaa ctcatagttg tgccaattca aacgacaccg | 1260 |
| ttcatctgaa ctacaaaaca gaataccgct atcaaattgg aacatggatt ctgtcaacaa | 1320 |
| ctcatcatta cctccgtctt atacaaccac tggtagaaca tatggacatt gtctgcaaat | 1380 |
| gctcacatgc ctcgagccac cgtgtacaac aacaaatgga aacggaatat caaacaatcg | 1440 |
| atgtctaaaa tgtatcgtag taaccatgtg ttcgatattc tccattgcag ctcatttggc | 1500 |
| tatcaccctg tcatgtataa ccttgattca atttattgac caaaaaatta tctatataaa | 1560 |
| ctgtactatt tatgctatca ccggatttct aattgccttc atcgtgcgtc ttacgataaa | 1620 |
| atcgtcagaa gtgctgacat caattggcaa accggcacaa tttatatttg ctttaatctc | 1680 |
| atccatagca gatacgctta ttacaagaaa tatgttaatt gacagtaatc catcttatgt | 1740 |
| aaaaatattg agagcaatag agatgacatc tttgatgtgc tttgtcatgc ttggagcatt | 1800 |
| cattgcatcc taccactatg tctgcttggc aacgtctgga gatttaactt ggaaagctgg | 1860 |
| gtttttgata ttgaccgccg gaacaattat cggaatatca gctccatatg gaaacatttc | 1920 |
| ctccctattc ggatttctat ttctatatac tatattagcc ataaacgttg taagggatgc | 1980 |
| aagtaaagca ctgatgaata catgctatta tcgcatttgt cgtgcaacga ctctacgcca | 2040 |
| tccctctcgc ctcggctgcg gtcgtatgtc ctcgactcaa gatgtcaatg caacgcatga | 2100 |
| agaagccata tcaagcgcag atacgattga tggtcagatt cctatggtag ttatgagcca | 2160 |
| cgcgacaggc gtattaattc cagttgttat tgccttgcag aggtacatga caaaggagac | 2220 |
| tgttagtttg acatcgactg atatgttaca gggagtctgt ggcgttttag tggggcgag | 2280 |
| tgtttcaata tttatcccgt cacgtcgcga cgaaagttta tcccgtccaa ttatcatttt | 2340 |
| attgtctata ataggagcaa tggccattac tttggcaggt tttggttttgg tactcgggcc | 2400 |
| aactttattt tccgcatgtg cagcagcttt gtcatgttat acctgcatta atataaggaa | 2460 |
| tgcaaataag ggaattaaac aattagcagc tgcctatgta gtgaaatcta tactgggatt | 2520 |
| tatcataact agtttacttg tttgtatatt agtagcgcta tcttgaccaa atcgttgttc | 2580 |
| acatcttggc catatacgta ttgatcgttg tttcgaaccg cgaataaaac tttcatacat | 2640 |
| actaaacgat ggagttgtgt tttatgagcg ttgaaaacaa aggtaccatc ggtttaaaac | 2700 |
| taagttgcat atcgtaatcc acaaaaatca ttttatacat catcccgaag agacaccaaa | 2760 |
| cgtaaccctc tacatatctt ccctcatgct cacgccgcgt gtgttacgag ctttggggtg | 2820 |
| gactggactc tttttttttgc ttttatctcc gagcaacgtc ctaggagcca gccttagccg | 2880 |
| ggatctcgaa acacccccat ttctatcctt tgatccatca acatttcaa ttaacggcgc | 2940 |
| gcctttaact gaggtacctc atgcaccttc cacagaaagt gtgtcaacaa attcggaaag | 3000 |

-continued

| | |
|---|---|
| taccaatgaa cataccataa cagaaacgac gggcaagaac gcatacatcc acaacaatgc | 3060 |
| gtctacggac aagcaaaatg cgaacgacac tcataaaacg cccaatatac tctgcgatac | 3120 |
| ggaagaagtt tttgttttcc ttaacgaaac gggaagattt gtttgtactc tcaaagtcga | 3180 |
| ccccccctcg gatagtgaat ggtccaactt tgttctagat ct | 3222 |

<210> SEQ ID NO 3
<211> LENGTH: 7316
<212> TYPE: DNA
<213> ORGANISM: Marek's Disease Virus 1

<400> SEQUENCE: 3

| | |
|---|---|
| ggatccaaaa ttctcaccat agtcaaccat ccactcagag ccatgcagtg tctttattta | 60 |
| aagtcacatg ggagattctc ttcggactcc gcctcacaaa gagtacaaca acatttccgg | 120 |
| gtagaacaaa agtaaagaat ttacggaagg cggagataga agctctgtta gacggagcgg | 180 |
| gtattgatag aacgtcatgc aaaactcaca aggatctcta caccctcttg atgaaaagca | 240 |
| agtcattatt tcgcaatatg cgctatgata ttcgacgccc gaagtggtac gacctattaa | 300 |
| gatctcgttt agacaaagag ttgggtatat atcatgatct ggtagatttg aatctgtgt | 360 |
| tggcggaaat tccgtcagca ctctggccac gcgtagaagg tgctgtagat tttcatcgtt | 420 |
| tataattatt ggaaccgaat gcgtcaaacc atatcaacga tggcagcatc gtcaaaaact | 480 |
| aatatgatgc agataatgcg aggatgtatt tgttatacga ctgtgtatag aatttggact | 540 |
| aataaaaatc gtaccgaagg actcactgca ttatgctatc tactttttcg aaatacatgc | 600 |
| ggtcaatact cggcacaata ttctacagta aacctctccg gaaaatccat ggctaaactt | 660 |
| tggggcctga acccagatat gattactgat acaatgttag caggtatgac caattccgca | 720 |
| tctgtaaccg gattatggcc atcttgccct tcggaccaac acatgctatg gaaagcgtta | 780 |
| ctcactacga ctctagcaaa attaagacac cgtctgggat atcatgctta ttatacacct | 840 |
| gtaaccatct atatcgacag tcaaactggg ttagttacag cttgcgaacc ggtatcagga | 900 |
| gaaagatcta tccctcgccc cggattattg aaaacggacg gaatgatcag cgttgaagag | 960 |
| tcatgtctta tctcgactgc catgaagcat gcggagggtg caccccctggc ccacattaaa | 1020 |
| ctgtcagccc ttaaacgtac ccgtcaaatt ccagagtttg acatgagaat tgaaatacag | 1080 |
| acaaaagaag aacgatttct tcgtgaatat aaaaaagtga acagcccata taagaaattt | 1140 |
| aaatgtgaca acaattcaaa tacaatattt aaagttgtgg acaatacgtt ggttttagac | 1200 |
| catttacagc ctccggtaag agcattgtct ctcgtcccca cgtcttttga ctgtttagtt | 1260 |
| acaacccccg ccgaattttc gcttgttgct ctattagcta cttatgcaaa atggcatgag | 1320 |
| aaactatact cttgtgataa cgaatcgaca aatattttgg tacctatatt aatgtacatc | 1380 |
| ggtcctgaaa ctaatccccg aggtgaagat gtagactata gttgtatcat cgggtttcca | 1440 |
| ggctggccaa ttgtgaaatc ctccaccgca aatcaaacag ctataaaaga tgcgatagat | 1500 |
| gcctatgtag atacgacgg cctgtggcca ttagctgggc ctagaacatt tcatctatta | 1560 |
| gctccgtggt ctcccgaaaa ccatccgttc cccatgatag acacgtccca cattttatct | 1620 |
| gtacattcta cggatatcag acacaaagca gccgatgaat ggacaacagg acgaataact | 1680 |
| tgtattttac gcgatccgac cctaatagaa aatgcagcga tcgccaaatt tgacttcagt | 1740 |
| gcattttttg caactttata tcttggcctc tttcccaccc attctcgatt acatgatgta | 1800 |
| gtgaaggcaa ggttaaaacg cgaaaaacca tggctcaaac ggcctatctt agaatttgga | 1860 |

```
ggtttgctta aaaaacttaa tgaagatgta tatcaatcta tcatctccat tgggaatcat    1920
attagtattg aggttgaggc taccgcatct tctcttatgt ttgctccctg tacttacatc    1980
aaagacggga tgtggggcac attcatggac aaatcaaaaa atgtcccacg tccgccaatg    2040
gatgatgagc gcgactttaa tatattgcgg aacgcgtgtg ctgagagcgc taataatttc    2100
gccgcgacaa tagggctgca gtttcccgac gaaattctac tagatctgcg tttggaaggc    2160
atttatacac atgcaatgtc atggaatgcc aactgttact ggctgtggaa taaatccaat    2220
catcataagg attttgtagg gtttcctaac caacctagat tgcaagtta tgcaaaacat     2280 ggtctttcta ctcttctgga aaaatatgc ataagcaatg atactgacga atctcttcaa     2340
acggttcgga aaaaaccca tgaagtgttc gaagagctgc tctccatagc gtttgatcac     2400
cgcagtgatg tgtccttttg gagctgtcct acagaattgt atgatgacac tcaatacatt    2460
gctgctctag gaatgaaggc agcagctaga tttgatacca gtggtttcaa tcgcgagact    2520
gtccaaactg tgacagcaga tggaaaaata gtttctgtta catgctctct ttttgaagga    2580 gaataatcc ttcctgccat agattgtatc gattatatga aaccaatact ggctgcattt     2640
tctagattat aatcaatgt tctgtcttct aaatgggaca atgttaacag atgattttt     2700 acgttcgata ttgagtcgta taggtttatg tttattaata ataaatgaca taaagttctg    2760
tttgcattat attttttatt ttcattttg gtatgtgtga aataaacatt cctccccct     2820 taaattgttt cgtccataat gccaccaatc acatattata tcacttaacc attttgttg    2880 gaaagctcca ttcaacaagc ctttgttgat tacgatagaa catttcctc gcgtagaaac     2940 tggtacctgg aacgcctcac ctaaattgtt acattcatat aaagatatta acacatcaca    3000
aactccatta gtagaactta aatgtttgta tataatgtag tgaggaagaa catgattact    3060
atcgaatgga ctaatagaac tcagttccat tagggtattt agtaaccaag tatttgtaat    3120
acataaaaat ctacgcattt tgcgcatcgg cgttactgtc gaccatgcat atttcagaaa    3180
actttgaagt tgaacatata gtgacgggtc ggatgagctg acgttccggt tttccaaata    3240
tgagatgagc aaacaaaggg caaatccaa aggttctgct ggatggtacg acacaaatct     3300
atattttaga agtgggggcg gtattcctat cgttttcacc acgtcctcca tagccgtgag    3360
aatcataaat atgaaacctt tgaacgcagg gttagctata cattgcgtgt aatatatatc    3420
actgcttatt tcttcgtcag tttcagttcc tgctaaaatc aaatgtaagc gtctaatgca    3480
gttcgctact cgaagtttat agacggagac acctgtaaac tgggtgggga ctccattaat    3540
ctctctgact tccatcatca tcctcgccat tggttgtcga ctgagttctt cgataatcgc    3600
gtctcgattc cctgttccat ctatggcgtt tataaccaga gcgtctagag tatcgctcac    3660
gtcgagagga tggagaatgg aagtcatttc ttcttccatg atggccgtca ggcaaatctt    3720
ctgcctcgcg ttgccttccc gaattatttc tgacgaggaa atatttcgcg atggctcttt    3780
ttacatcggc attaaagatt agtgctaaat catccagata acgtgaata cgtgtctttt     3840 caaataccga attgcataac tcctcctctg atttataaac ctcgtgattc gttactattg    3900
gcccaatatc ataaatattc aatacggaaa aaaagtaagg agcgagtagt aaagttatcg    3960
cactgttcga gtaggaaatt gaaacctcat gaccctgatt attggtagct cgtgtcaatt    4020
taaaacatcg cagcatttcc tgttcccaaa gttcagaaag tcttttcaag tctacatcat    4080
acgcaggtat atatcttgac tgaaaactat tagcaacata ggaatcatca tccataactt    4140
cacctacatc aataacatca tgtttaaggt cacgcgccaa agtttctaat gtcgggctgt    4200
actgagaatt gcccatatca gtgtgtgcct gttttgagat aagatgttca gtacgaactc    4260
```

-continued

```
tgtcgagttc taattctttg gaacaaagtt ttgctagcaa atctttattg gcagctttca    4320
agccttcaac ggtgttaaac aatttattca catagccttc tagcatctcg tttatacttg    4380
ttacaacaga cgaatggaat gcatcccgaa ttttaatggt attacgtcga gtttcctcgg    4440
ttgtagaaga ttgtgcccga ttggattggc cgaaacccgg ctgagatgta tcgatcgaag    4500
cagcatccaa taaatgcccg ctcgtttctt ccaaatagtc tcgaaccgtg tcagtaatat    4560
ctcccacatg acgcatacct ttaagaccaa taatcagttt gactaatctg gatgcagcag    4620
aacttgctgc atttttctggt tgatctccca aaactttgtc gatgactcgt tgggcccctg    4680
ctaccccctt acatccatca tcgcgttttg caataagaac ttttacagga gccgtgttga    4740
caagtcgaca taaagttgca tgttgacgca aatcatgaca ttcaataatc tccttgtata    4800
ttcgttgcat tggcgaatca aaaataactc cgccatcgtt cattactggc ctccagataa    4860
caatacattc cccacgctca ccactcaata tatcctttac ccgaagttct cgtttaaaga    4920
aattatattc tatcaatgtt ctgtcatatt cgagaatgct tactgccgac atcgaattcg    4980
ataagtaatt cacaatttgt tttccacgag ccataacact atcgacgact cgaagtctac    5040
tggaggcatc atgaaatgcc cagtttggaa aaacagttga tctgcctgcg catgtaggta    5100
tagaacttgt tgcccttgca gaacgatcat gtctaacaac tggaacgata ccaaggcaac    5160
aaatccaatc tatatatttg gaaaaactgg aagtgtttat attggccgta gtaaagcaag    5220
aaattagctg acgagccaaa tttatcaatg tagttttgcag agttttgcgc catgttacaa    5280
aaacattttc tgctacctta acagcttctg cttcactatg cataccatat gttctggcaa    5340 gttttttttgc tgacatccca cgcatgtcag catgccgtat ccaatcattt tttagatcgt    5400
catatctaac cgcatccagg ctaagggtga aatagtatt ttgaatctgt cgaattgcgg    5460
tttctgtaga tcttacggag ttatatatac cctggccatc agtatatcct aatcgacctg    5520
cgaggatctc cttaaacatc cgtgtctgac gagtaggatg gatcacaatc cactgattct    5580
ccatacactg ttttgatgag acgttgttaa agtatctcg ttgcgacata accgattcga    5640
agtccggatg attaattttt ctactattta aatcgtaagg cgctcttcga tcatagccat    5700
ccattacaag aaatacgaca cgcctctaaa ataattcaag aaaaattttta atttttgcga    5760 gtctattgaa aatgtcacag gaatcgaatg acttattttg cgaagcgacc tatttaaatt    5820
ttaccgccat gcatggaata caatctataa ttactcgtgt aagagctctt gcggacgcga    5880
cgctgagcga tgaattgatt ccaccgttat cctatttat agaagcttcg aatcatgaaa    5940
accctgtaga attagaagca cgagacttgc cattcgctgt ttatttgata agtggcaatg    6000
cgggatctgg aaagagcaca tgcatacaaa cattatcaga gattttggat tgcattatta    6060
ctggtacaac aaaagttgca tctcaaaaca tatattgcaa actcagtaat tcctatacat    6120
cgccacatat aaacactata ttccaggaat ttgggtttaa aggcaaccat gttcaagcca    6180
atttgggtaa atggcaatat gtatgttcga ccagtccacc tacaatgaaa gaattacaaa    6240
aaaaggatat tgtatattat tgggaagtcc tgtccgatat aacgaaaagt atgctgaaag    6300
ttttggattc ggagacaggt ccagggaaat tgatgtaat acggacatta gaagatctgc    6360
tgggaaaacc tagaggaaac ttgtcttgga tgactttcgg gatacatgga tcactgccat    6420
catttacacg cagtaatata atcatcatcg atgaagccgg attgttgggg aaatatttac    6480
ttacggctat tgtatactgt tggtggctta ccaatgccgt gtatcgtact ccacaatata    6540
aaagagggtt aaaaccagta ttaatatgtg tcgggtcgcc tacacaaaca agttcattgg    6600
```

```
-continued aatcgacatt tgaacatagc aaactgaggt gtaatgtaag aataagcgaa aatattctga    6660
cttatattat atgcaatcaa acattacgat catatttaga cttatccaat aattgggcaa    6720
tatttattaa taataaacgc tgtacagaac ccgaatttgg agatcttctc aaaacattgg    6780
aatatggact tcctataacg gaggagcatg cccgaatggc agataacttt gttgttccgg    6840
aagcatttat caataatccg gcgaacctac ctggctggac acgtttatat tcatctcata    6900
aggaagtcag tacatatatg agtagattac atgattactt gaaaacctcc ggcaacaata    6960
agtttgtggt gtttactctg cctgcatata cttttataag tttggagaat tttgaacgct    7020
atcgtacggc tgccaatcaa cctcatatta cacttgagaa atggctcaat gtcaatgcgg    7080
ggcgtttgag caactggtca caaagccgtg atcaagacgc aacacaaact agatgcgaaa    7140
ttagaagcca acaaggtctt gcaatctcat gttctgacat aacttacgta ctgaatagtc    7200
aagtggctgt gactacacga cttaggaaat gggttttcgg tttttgcggc acctttgaga    7260 atttttttatc tgtcttaaaa gatgactcgt ttataaaaac acacggagaa ggatcc       7316
```